(12) United States Patent
Rittgers et al.

(10) Patent No.: US 7,744,642 B2
(45) Date of Patent: Jun. 29, 2010

(54) PROSTHETIC VENOUS VALVES

(75) Inventors: Stanley E. Rittgers, Stow, OH (US); M. Michelle Evancho-Chapman, Kent, OH (US); Matthew T. Oberdier, Pittsburgh, PA (US); Steven P. Schmidt, Akron, OH (US); Stephanie T. Lopina, North Canton, OH (US)

(73) Assignees: Biomedical Research Associates, Inc., Akron, OH (US); The University of Akron, Akron, OH (US)

( * ) Notice: Subject to any disclaimer, the term of this patent is extended or adjusted under 35 U.S.C. 154(b) by 163 days.

(21) Appl. No.: 11/282,515

(22) Filed: Nov. 18, 2005

(65) Prior Publication Data

US 2006/0111773 A1 May 25, 2006

Related U.S. Application Data

(60) Provisional application No. 60/629,568, filed on Nov. 19, 2004.

(51) Int. Cl.
*A61F 2/24* (2006.01)
(52) U.S. Cl. ............... 623/1.24; 623/2.12; 623/2.17
(58) Field of Classification Search ........ 623/1.24–1.26, 623/2.12–2.19, 2.1, 2.2–2.33, 217
See application file for complete search history.

(56) References Cited

U.S. PATENT DOCUMENTS

| | | | |
|---|---|---|---|
| 3,717,883 A | 2/1973 | Mosher | |
| 4,222,126 A * | 9/1980 | Boretos et al. ............. | 623/2.19 |
| 4,253,201 A | 3/1981 | Ross et al. | |
| 4,491,986 A * | 1/1985 | Gabbay .................... | 623/2.18 |
| 4,605,407 A | 8/1986 | Black et al. | |
| 4,759,758 A | 7/1988 | Gabbay | |
| 4,759,759 A | 7/1988 | Walker et al. | |
| 5,500,014 A * | 3/1996 | Quijano et al. ............. | 623/1.24 |
| 5,554,185 A | 9/1996 | Block et al. | |
| 5,562,729 A | 10/1996 | Purdy et al. | |
| 5,824,061 A | 10/1998 | Quijano et al. | |
| 6,029,671 A | 2/2000 | Stevens et al. | |
| 6,071,305 A * | 6/2000 | Brown et al. ............... | 623/1.43 |

(Continued)

OTHER PUBLICATIONS

Dalsing et al., "A multicenter, phase I evaluation of cryopreserved venous valve . . . ," Journal of Vascular Surgery, vol. 30 #5, pp. 854-866, (1999).

(Continued)

*Primary Examiner*—David H Willse
*Assistant Examiner*—Megan Wolf
(74) *Attorney, Agent, or Firm*—Fay Sharpe LLP

(57) ABSTRACT

A prosthetic venous valve includes a frame and leaflets. The frame includes: (i) a generally hollow base disposed at a blood inflow end; (ii) a plurality of struts connected with the base and extending generally parallel to a direction of forward flow of blood from the generally hollow base to a blood outflow end; and (iii) inwardly oriented flanges disposed at the blood outflow ends of the struts. The leaflets are disposed in gaps between the struts and are supported by the frame. The leaflets are arranged to close into the vein lumen to substantially seal against backflow of blood from the blood outflow end to the blood inflow end. The inwardly oriented flanges of the struts enhance the sealing.

16 Claims, 22 Drawing Sheets

U.S. PATENT DOCUMENTS

| | | | |
|---|---|---|---|
| 6,086,612 A * | 7/2000 | Jansen | 623/2.17 |
| 6,283,995 B1 * | 9/2001 | Moe et al. | 623/2.19 |
| 6,440,164 B1 * | 8/2002 | DiMatteo et al. | 623/1.24 |
| 6,958,076 B2 | 10/2005 | Acosta et al. | |
| 7,402,171 B2 | 7/2008 | Osborne et al. | |
| 7,416,557 B2 | 8/2008 | Drasler et al. | |
| 7,569,071 B2 | 8/2009 | Haverkist et al. | |
| 2002/0052651 A1 * | 5/2002 | Myers et al. | 623/2.15 |
| 2002/0177894 A1 * | 11/2002 | Acosta et al. | 623/1.24 |
| 2002/0183840 A1 * | 12/2002 | Lapeyre et al. | 623/2.22 |
| 2003/0036794 A1 * | 2/2003 | Ragheb et al. | 623/1.15 |
| 2003/0093147 A1 * | 5/2003 | Ogle et al. | 623/2.12 |
| 2005/0075713 A1 * | 4/2005 | Biancucci et al. | 623/1.11 |
| 2005/0186241 A1 * | 8/2005 | Boyle et al. | 424/423 |
| 2005/0228482 A1 * | 10/2005 | Herzog et al. | 623/1.15 |

OTHER PUBLICATIONS

Kumins et al., "Free tissue transfer provides durable treatment for . . . ," Journal of Vascular Surgery, vol. 32 #5, pp. 848-854, (2000).

DeLaria et al., "Hemodynamic evaluation of a bioprosthetic venous prosthesis," Journal of Vascular Surgery, vol. 18, #4, pp. 577-586, (1993).

Hill et al., "Development of a prosthetic venous valve," Journal of Biomedical Materials Research, vol. 19, pp. 827-832, (1985).

Taheri et al., "Experimental Prosthetic Vein Valve," The American Journal of Surgery, vol. 156, pp. 111-114, (1988).

Van Cleef, "A Vein Has a Preferential Axis of Flattening," Elsevier Science Publishing Co., Inc., Dermatol Surg Oncol 19, pp. 468-470, (1993).

Taheri et al., "Experimental Prosthetic Vein Valve . . . ," The Journal of Vascular Diseases, vol. 46, #4, pp. 299-303, (1995).

Bemmelen et al., "The Mechanism of Venous Valve Closure," Arch Surg, vol. 125, pp. 617-619, (1990).

Reeves et al., "Mechanical characteristics of lyophilized human . . . ," Journal of Vascular Surgery, vol. 26, #5, pp. 823-828, (1997).

Criado et al., "Venous Disease," Curr Probl Sur., pp. 339-399, (1991).

Burkhart et al., "Experimental repair of venous valvular insufficiency . . . ," Journal of Vascular Surgery, vol. 26, #5, pp. 817-822, (1997).

Wang et al., "In vitro performance of venous valve prostheses . . . ," ASAIO J, vol. 38, #3, pp. 213-215, (1992)—Abstract.

* cited by examiner

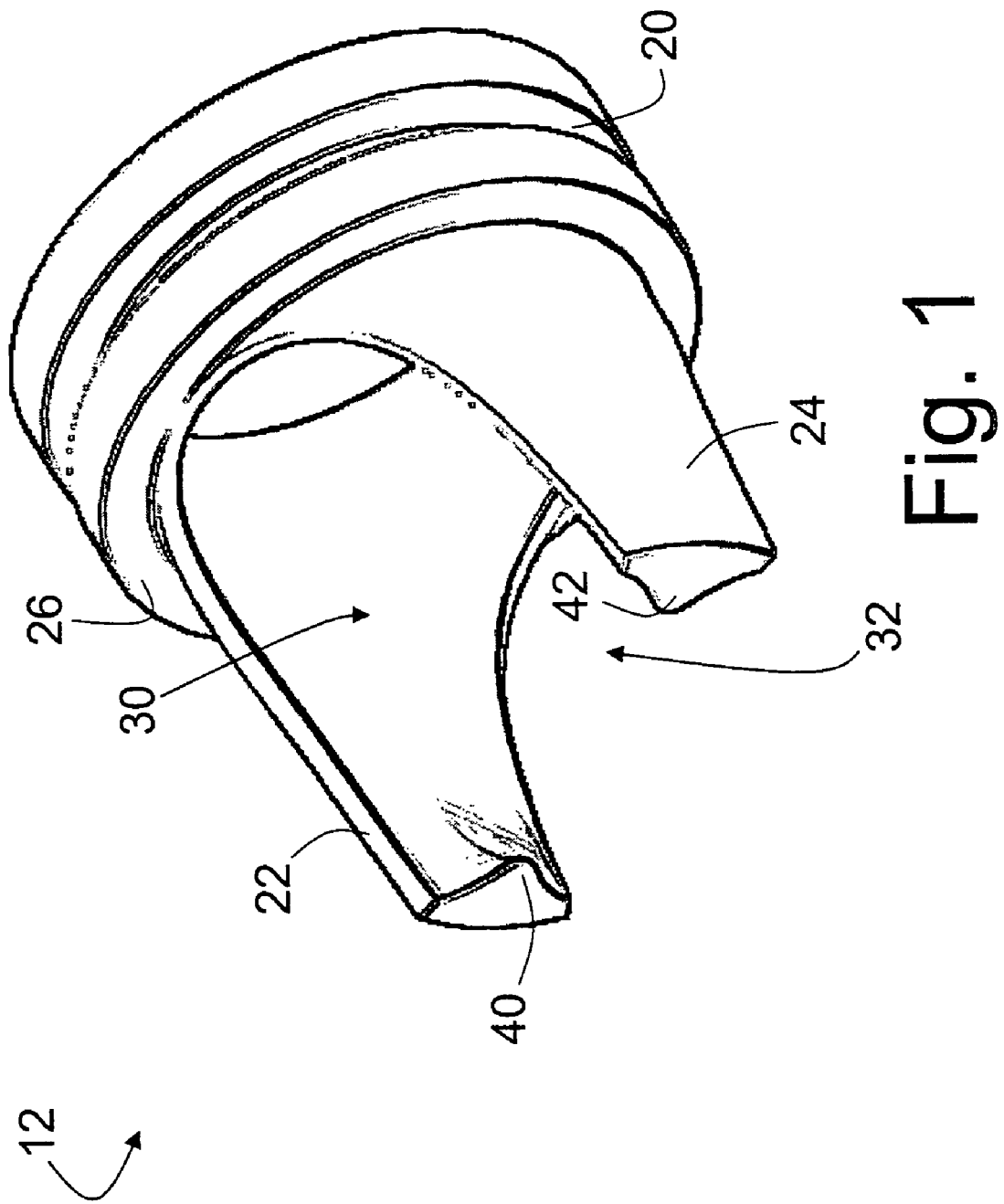

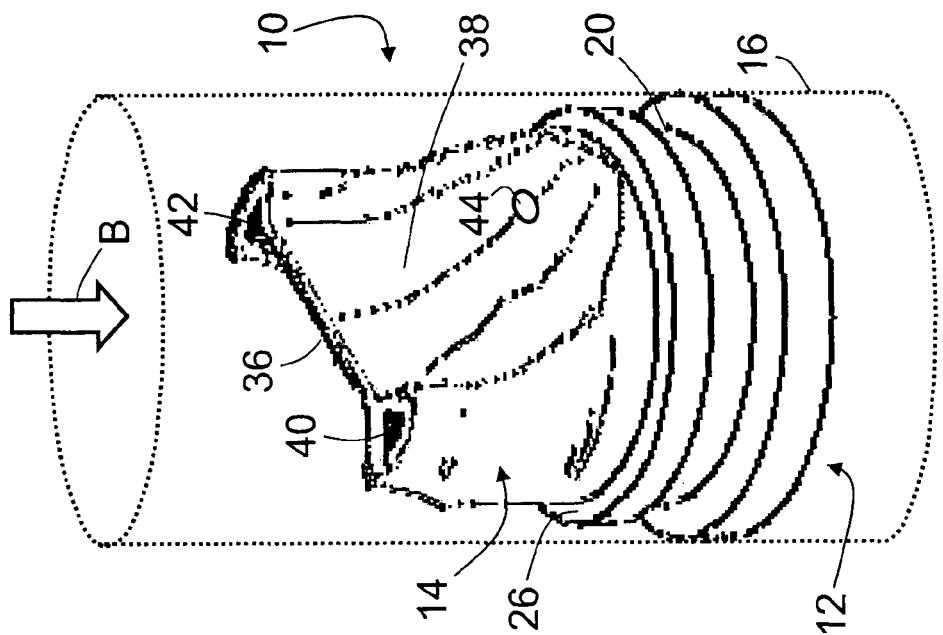
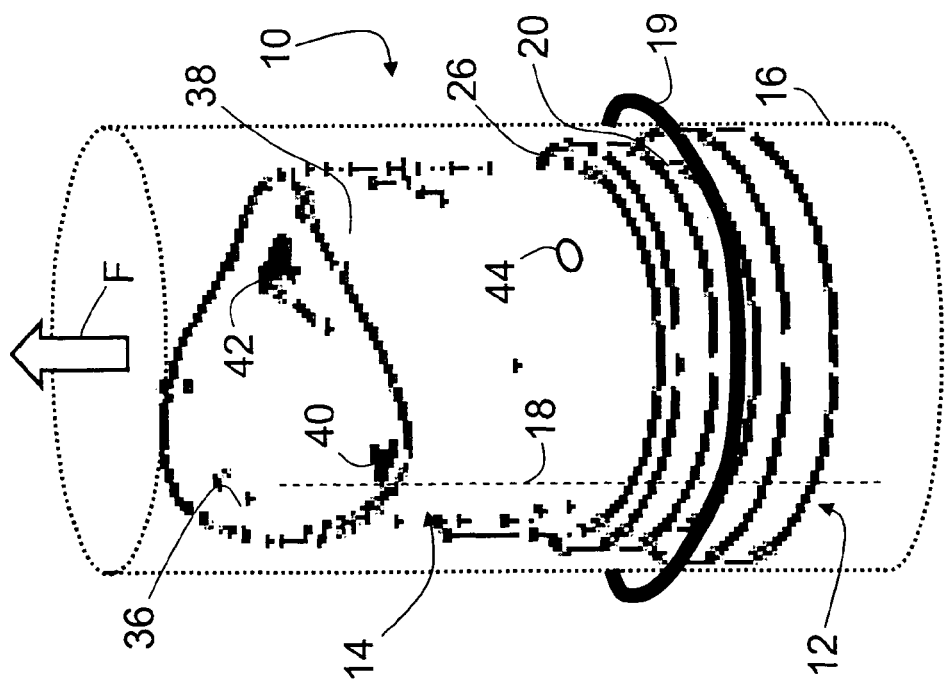

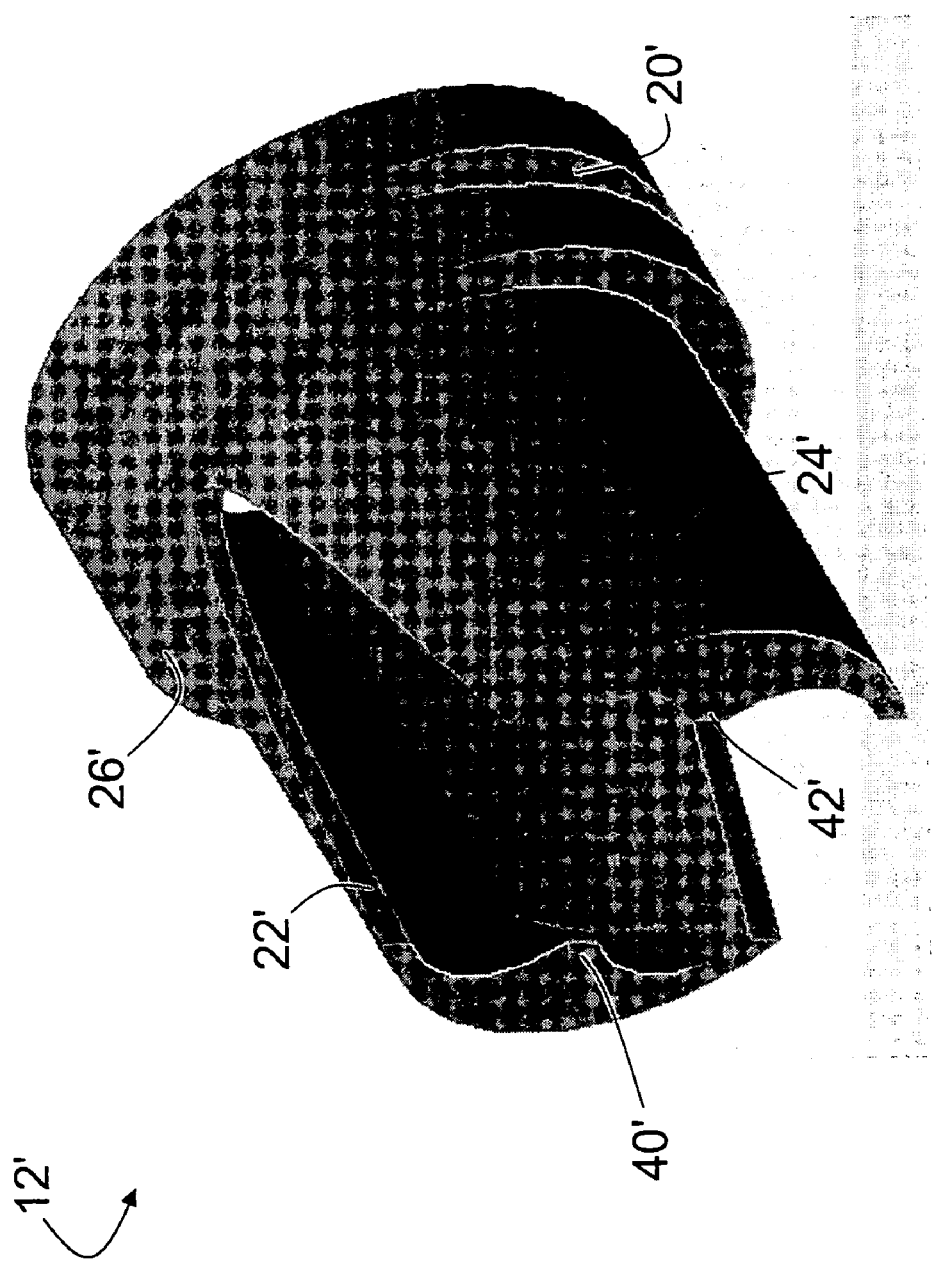

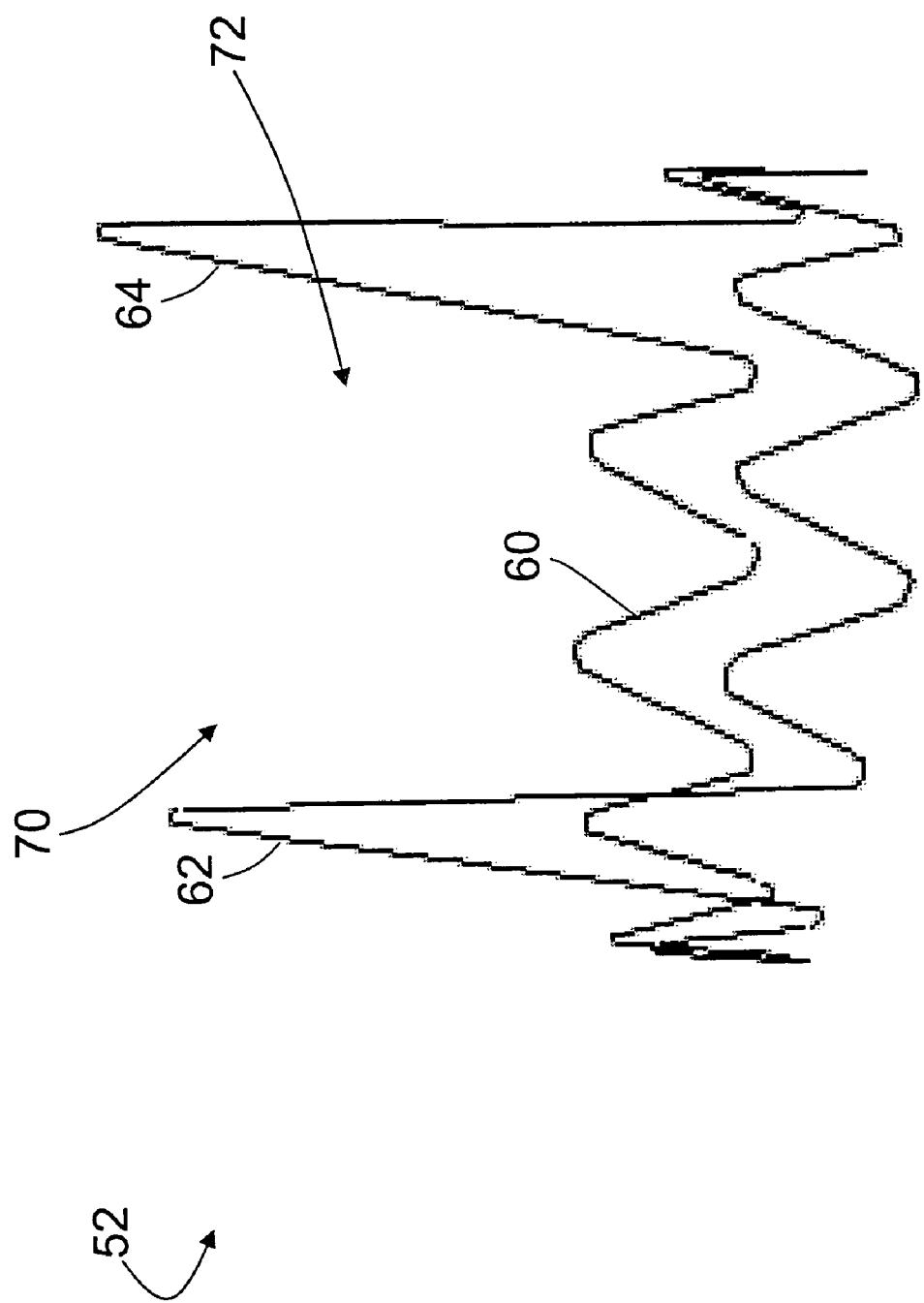

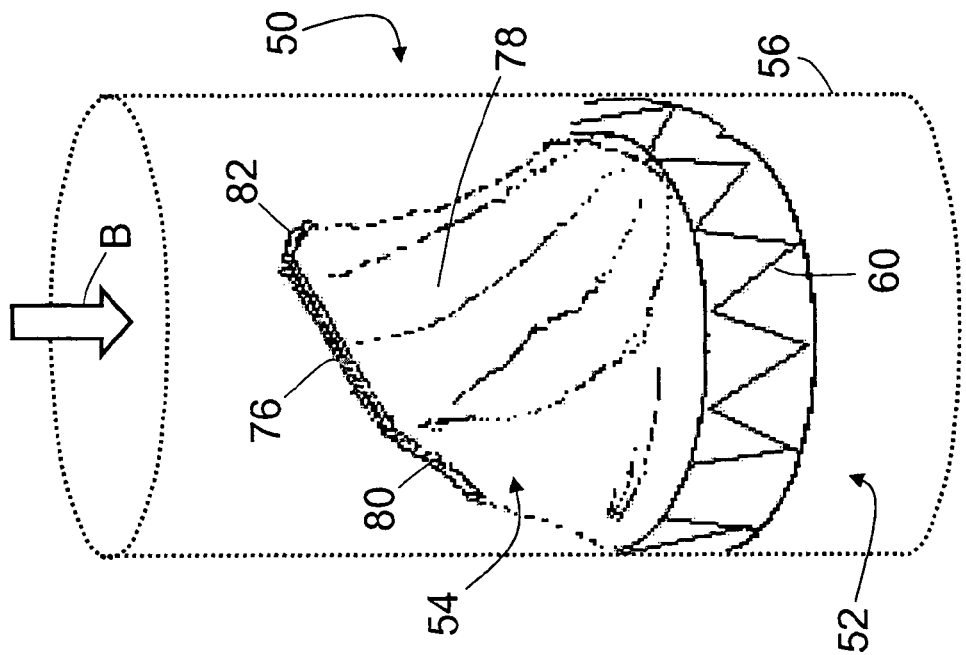
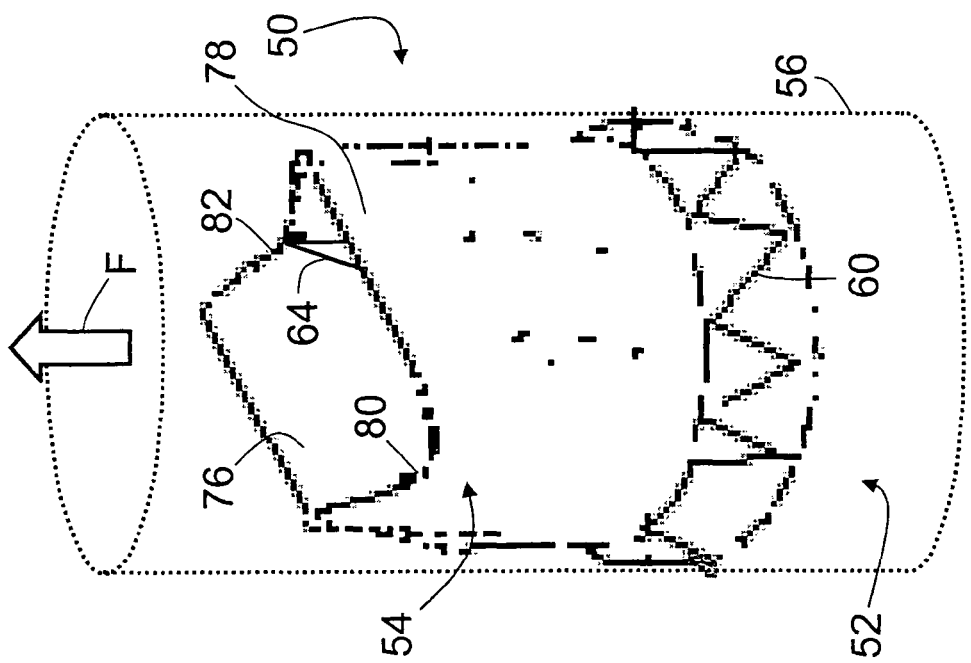

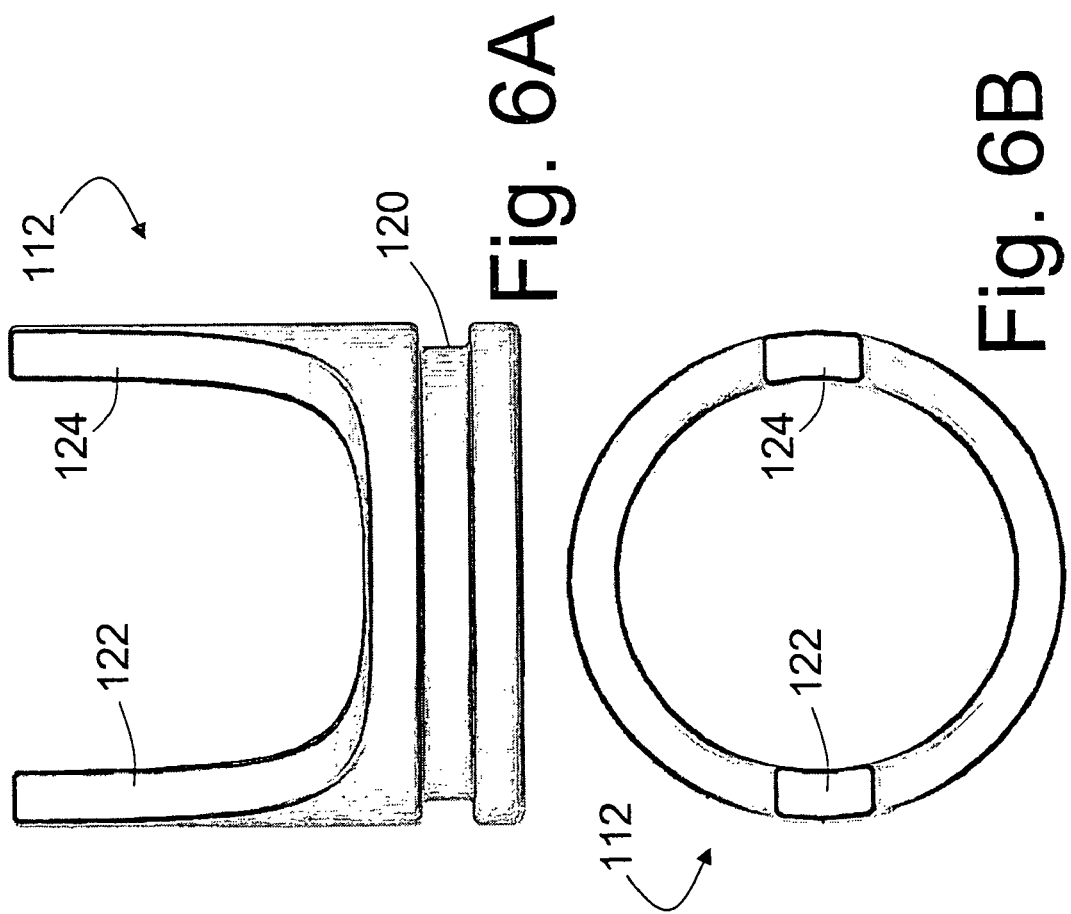

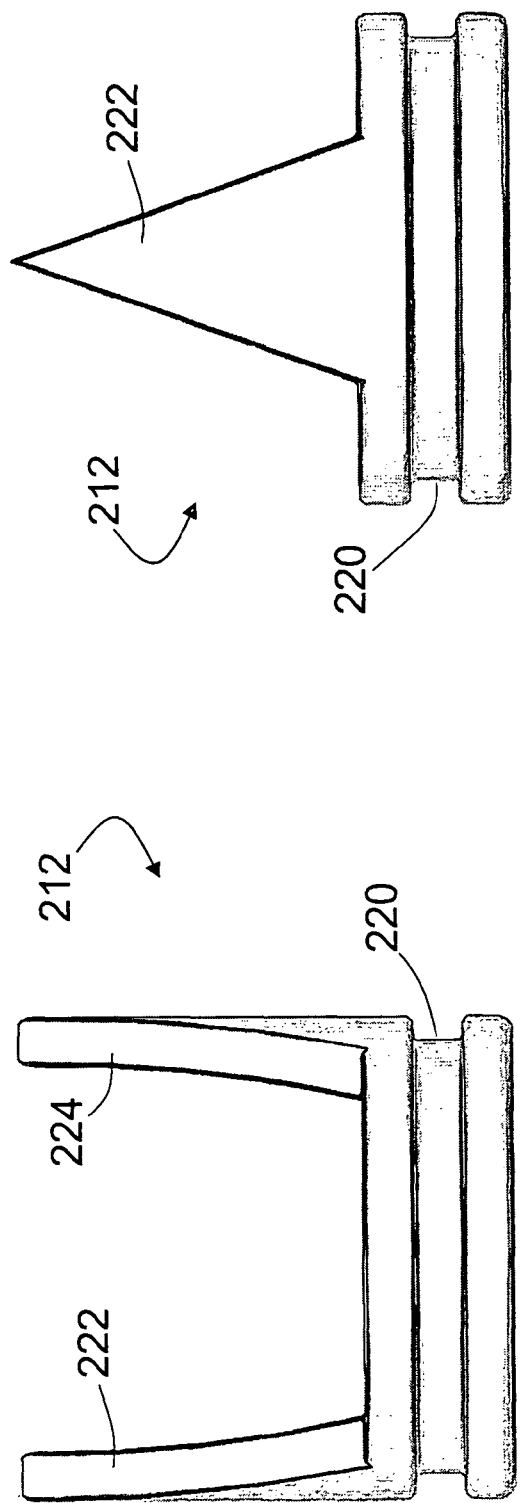

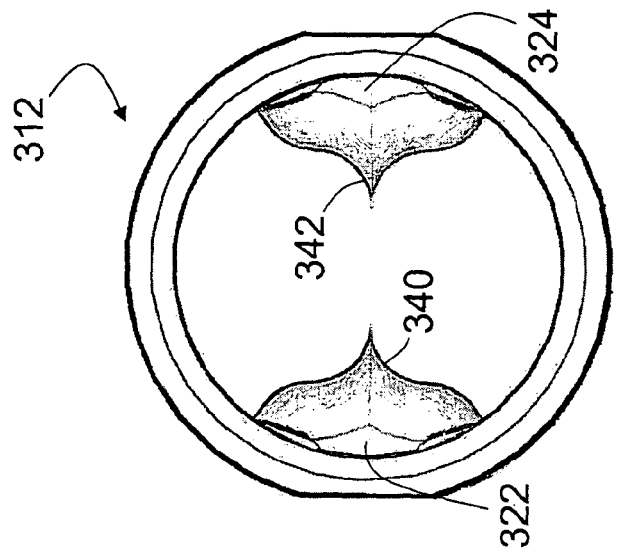
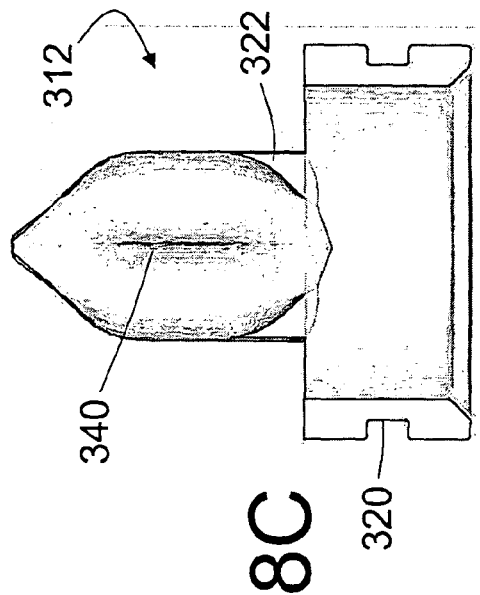
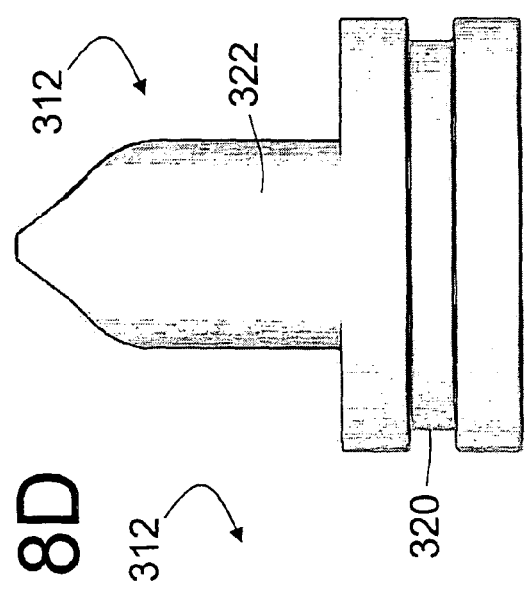
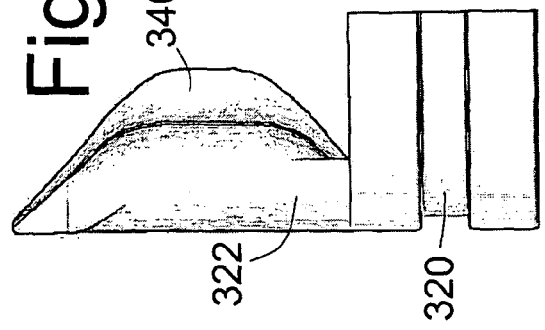

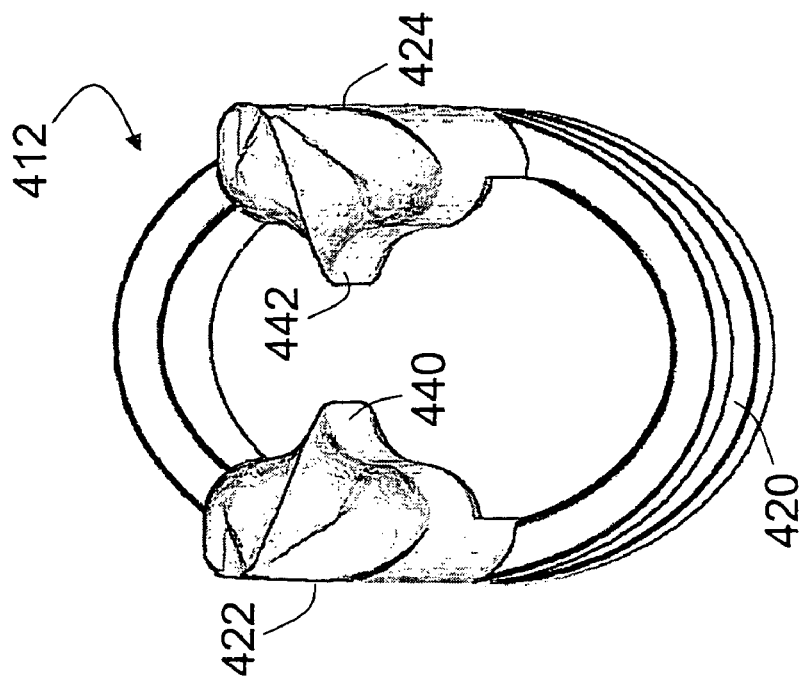
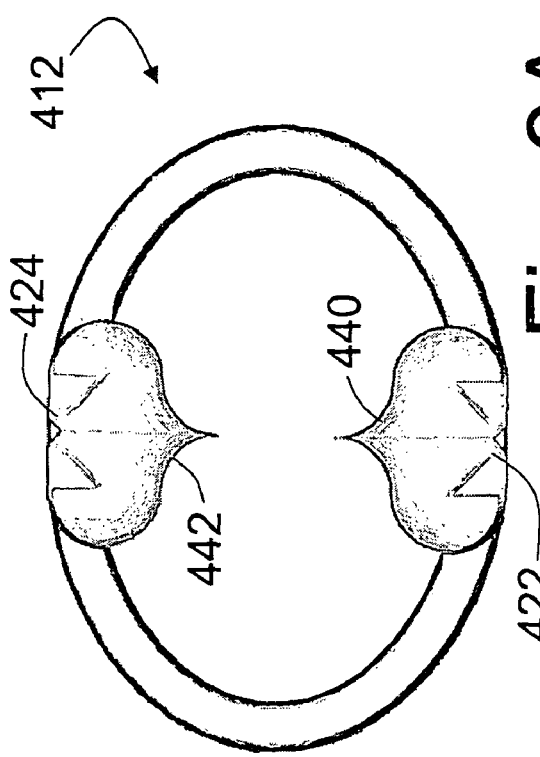
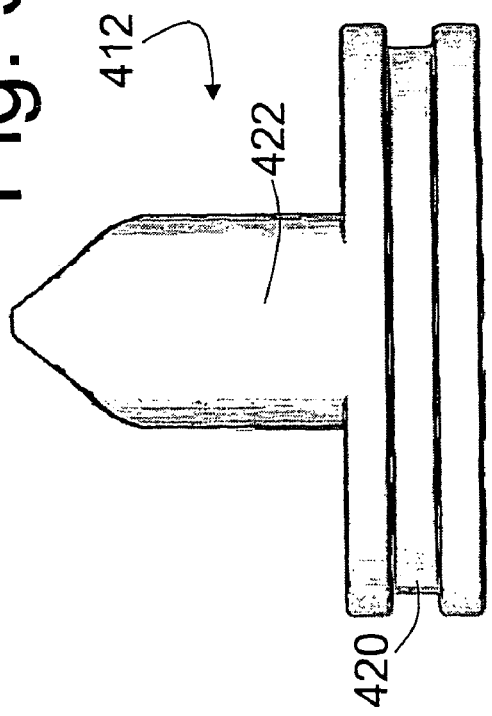
Fig. 9A
Fig. 9B
Fig. 9C

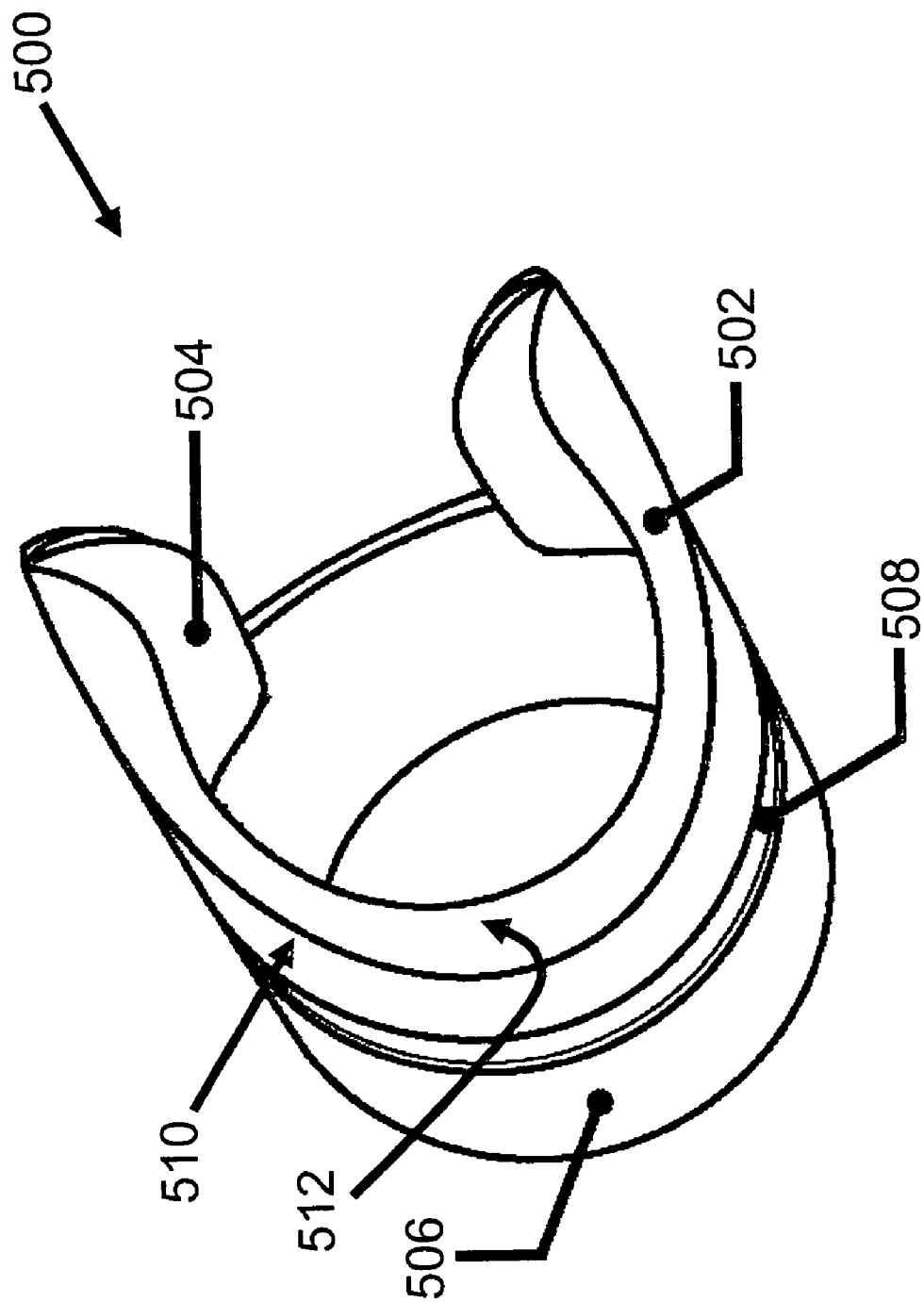

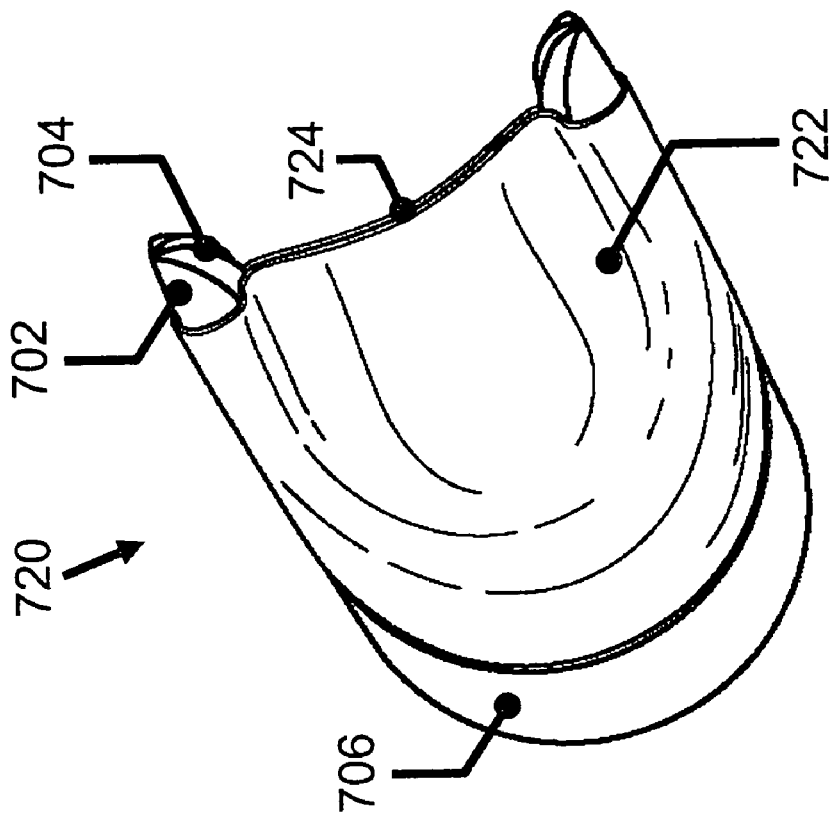
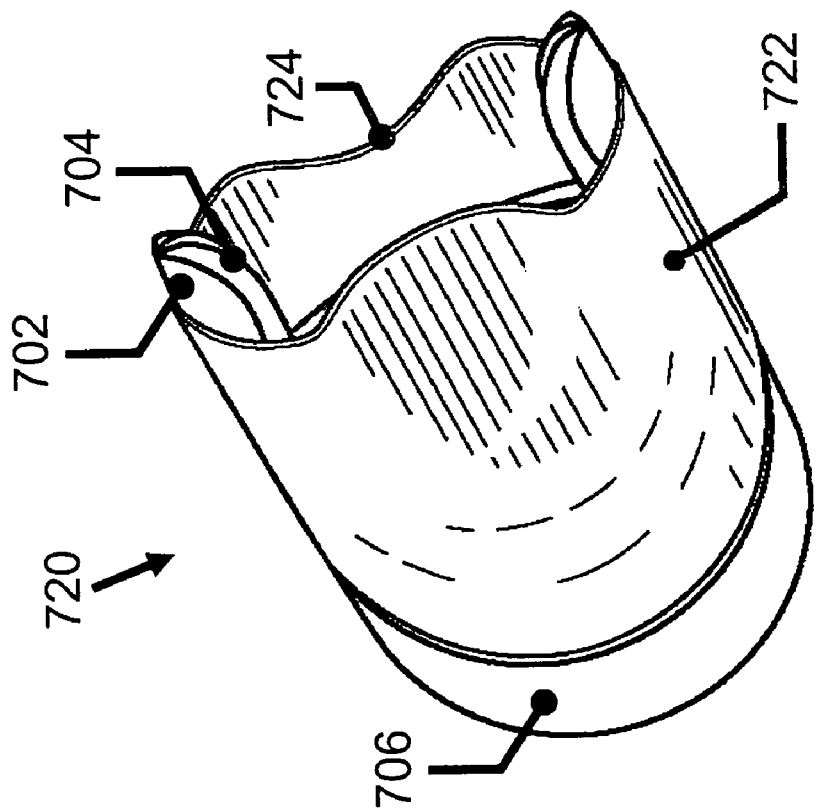

PROSTHETIC VENOUS VALVES

This application claims the benefit of U.S. Provisional Application No. 60/629,568, filed Nov. 19, 2004. U.S. Provisional Application No. 60/629,568 is incorporated by reference herein in its entirety.

BACKGROUND

The following relates to the medical arts. It especially relates to prosthetic venous valves for treatment of chronic venous insufficiency, and will be described with particular reference thereto. However, the following will also find application in treatment of venous blood flow problems generally.

Chronic venous insufficiency is a pathologic condition of the skin and subcutaneous tissues of the lower extremities that results from prolonged stasis of venous blood flow. The venous stasis condition is typically brought on by an abnormal venous hypertension that upsets the normal equilibrium of capillary fluid exchange. This venous hypertension manifests pathologically as changes in the skin and subcutaneous tissues, and can lead to conditions such as edema, pigmentation, dermatitis, induration, stasis cellulitis, and stasis ulcerations. Chronic venous insufficiency is typically difficult to treat, often disabling, and negatively impacts the patient's quality of life.

The most common cause of venous hypertension is degradation of the functionality of one or more venous valves in the deep veins. These valves ordinarily function as "check valves" to prevent backflow of venous blood. However, degraded venous valves are unable to completely block backflow of venous blood, resulting in development of venous hypertension and stasis. The venous hypertension and stasis, in turn, leads to additional distention of the vein and further degradation of the valve.

Various medical therapies are used to treat chronic venous insufficiency. In the lower extremities, compression stockings or boots are used to promote flow of venous blood toward the heart. Surgical interruption of perforator veins in the regions of hypertension has been used to decrease the symptoms of chronic venous insufficiency. In some cases, the degraded venous valve can be surgically repaired.

In another approach, a vein valve is transplanted from a healthy region into the region suffering from chronic venous insufficiency. For example, venous valves in the arm can be transplanted into the leg. This approach presupposes that the patient has healthy venous valves available for transplant. Patients suffering from chronic venous insufficiency often also suffer from other vascular and/or coronary diseases, and so it may be undesirable to transplant healthy venous tissue that may be needed for later bypass procedures.

To address these concerns, both bovine and sheep vein valves have been used as substitutes for human vein valves in transplantation procedures. However, availability of suitably prepared animal vein valves, interspecies tissue compatibility, and other concerns arise in such procedures.

Attempts have also been made to replace degraded venous valves with prosthetic replacements. Existing prosthetic venous valve designs have generally been modeled on prosthetic cardiac valve designs. Prosthetic cardiac valves are normally closed, and only open in response to the substantial blood pressures generated by the beating heart. Such normally closed designs have been successful in the cardiac environment; however, they generally exhibit poor performance in the low flow, low pressure venous system that fosters thrombosis and intimal hyperplasia of implanted prosthetic devices.

Venous blood pressures are lower than those encountered in the heart, and the venous valve must remain open under low blood pressure and flow. Infrequent venous valve cycling and low venous blood pressure and flow produces substantial residency times for blood contacting the prosthetic venous valve. Flow resistance caused by a normally closed or incompletely open venous valve replacement further increases blood residency time and can lead to blood clotting.

Acosta et al., U.S. Pat. No. 6,958,076 (previously published as U.S. Publ. Appl. 2002/0177894 A1, which is incorporated herein by reference in its entirety), discloses various normally open venous valves that represent substantial improvements over previous normally closed prosthetic venous valves that are modeled after heart valves. These normally open venous valves more closely functionally mimic natural human venous valves. They provide low resistance to blood flow in the normal open condition, which reduces the residency time of blood contacting the venous valve replacement. This in turn reduces the likelihood of blood clot formation at or near the venous valve replacement.

The following contemplates improved apparatuses and methods that overcome the above-mentioned limitations and others.

BRIEF SUMMARY

According to one aspect, a prosthetic venous valve is disclosed. A frame includes: (i) a generally hollow base disposed at a blood inflow end; (ii) a plurality of struts connected with the base and extending generally parallel to a direction of forward flow of blood from the generally hollow base to a blood outflow end; and (iii) inwardly oriented flanges disposed at the blood outflow ends of the struts. Leaflets are disposed in gaps between the struts and are supported by the frame. The leaflets are arranged to close into the vein lumen to substantially seal against backflow of blood from the blood outflow end to the blood inflow end. The inwardly oriented flanges of the struts enhance the sealing.

According to another aspect, a prosthetic venous valve is disclosed. A generally hollow frame includes a base at a blood inflow end and struts extending from the base toward a blood outflow end. Leaflets are disposed in gaps between the struts. The leaflets are arranged to close into the vein lumen to impede or block backflow of blood. A drug is disposed on or in at least one of the frame and the leaflets.

According to another aspect, a prosthetic venous valve is disclosed. A generally tubular leaflets member is supported by a generally hollow frame. The generally tubular leaflets member defines leaflets arranged to lie along an inner vein wall during forward flow of blood from a blood inflow end to a blood outflow end and are arranged to close into the vein lumen to impede or block backflow of venous blood from the blood outflow end to the blood inflow end. At least one of the frame and the generally tubular leaflets member include an inward tapering in the general direction from the blood inflow end to the blood outflow end.

According to yet another aspect, a prosthetic venous valve is disclosed. A frame includes: (i) a generally hollow base disposed at a blood inflow end; (ii) a plurality of struts connected with the base and extending generally parallel to a direction of forward flow of blood from the generally hollow base to a blood outflow end; and (iii) at least one halo ring spaced apart from the base and oriented generally transverse to and connecting with the struts. Leaflets are disposed in gaps between the struts and are supported by the frame. The leaflets are arranged to close into the vein lumen to impede or block backflow of blood from the blood outflow end to the blood inflow end.

Numerous advantages and benefits will become apparent to those of ordinary skill in the art upon reading and understanding the present specification.

BRIEF DESCRIPTION OF THE DRAWINGS

The drawings are only for purposes of illustrating preferred embodiments and are not to be construed as limiting.

FIG. 1 shows a polymer frame for a prosthetic venous valve.

FIG. 2A shows a prosthetic venous valve, including the polymer frame of FIG. 1, implanted into a vein. FIG. 2A shows the prosthetic venous valve in its normally open position.

FIG. 2B shows the prosthetic venous valve of FIG. 2A in its closed position responsive to a backflow of venous blood.

FIG. 3 shows another embodiment of a polymer frame for a prosthetic venous valve, having narrower gaps for the leaflets.

FIG. 4 shows a wire frame for a prosthetic venous valve.

FIG. 5A shows a prosthetic venous valve, including the wire frame of FIG. 4, implanted into a vein. FIG. 5A shows the prosthetic venous valve in its normally open position.

FIG. 5B shows the prosthetic venous valve of FIG. 5A in its closed position responsive to a backflow of venous blood.

FIGS. 6A, 6B, and 6C show side, top, and perspective views, respectively, of another polymer frame for a prosthetic venous valve.

FIGS. 7A, 7B, and 7C show first and second side views and a perspective view, respectively, of another polymer frame for a prosthetic venous valve.

FIGS. 8A, 8B, 8C, and 8D show side, top, one-half side, and side-sectional views, respectively, of another polymer frame for a prosthetic venous valve.

FIGS. 9A, 9B, and 9C show top, side, and perspective views, respectively, of yet another polymer frame for a prosthetic venous valve.

FIG. 10 shows a perspective view of a frame of a first prototype valve type design.

FIGS. 17A and 17B show perspective views of the third prototype valve type including the frame of FIG. 16 and a generally tubular leaflets member in the open and closed positions, respectively.

DETAILED DESCRIPTION OF PREFERRED EMBODIMENTS

Figure 11B:
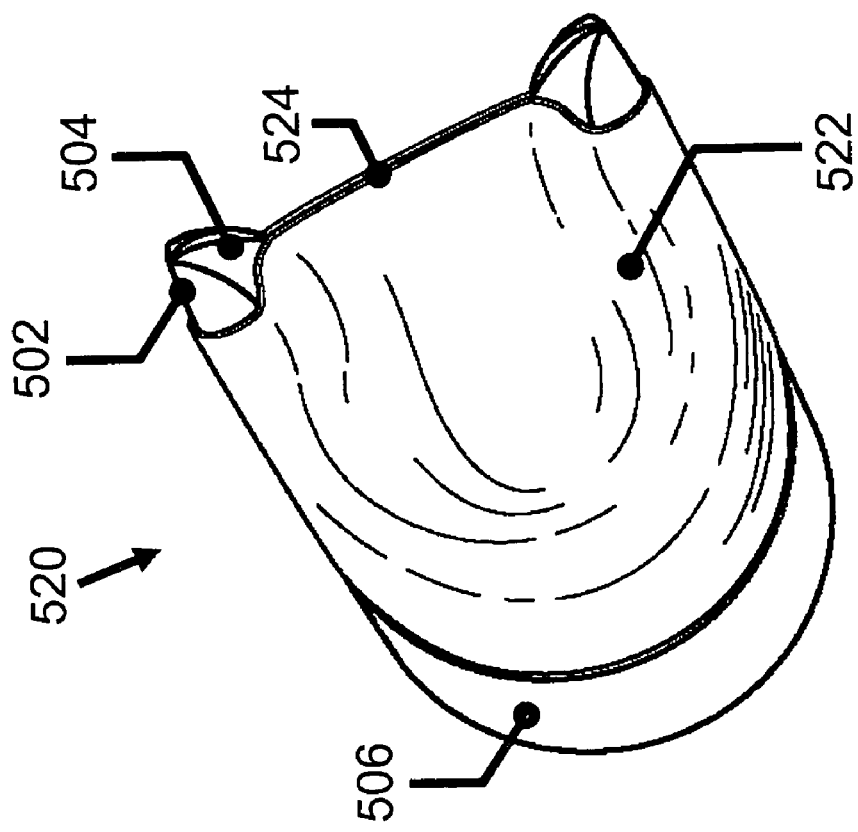
FIGS. 11A and 11B show perspective views of the first prototype valve type including the frame of FIG. 11 and a generally tubular leaflets member in the open and closed positions, respectively.

With reference to FIGS. 1, 2A, and 2B, a normally open prosthetic venous valve 10 includes a generally hollow polymer frame 12, surrounded by a flexible generally tubular leaflets member 14. The prosthetic venous valve 10 is implanted into a vein 16 (shown in phantom). When implanted, the polymer frame 12 is arranged coaxially with the vein, and the generally tubular leaflets member 14 is arranged coaxially with the vein on the outside of the generally hollow polymer frame 12, so that the prosthetic venous valve 10 does not substantially impede venous blood flowing in its normal direction F indicated in FIG. 2A.

The prosthetic venous valve 10 is secured inside the vein using substantially any medically accepted implantation procedure. In one suitable approach, a longitudinal slit 18 (indicated by a dashed line in FIG. 2A) is surgically cut into a wall of the vein 16, and the vein wall is elastically distended at the slit 18 to form a longitudinally oriented opening. The prosthetic venous valve 10 is inserted into the longitudinally oriented opening, and the longitudinally oriented opening is sutured closed. A securing suture 19 (shown in FIG. 2A) is tied around the outside of the vein 16 aligned with a groove 20 of the frame 12. When the suture 19 is tightened (FIG. 2A shows the suture 19 before it is tightened), it compresses the vein into the groove 20 to secure the valve 10 inside the vein 16. Advantageously, this approach is partially self-aligning in that the tightening of the suture 19 tends to orient the prosthetic venous valve 10 along the lumen of the vein 16.

In some embodiments, the frame 12 is a polyetherurethane base (Elasthane™, The Polymer Technology Group, Berkeley, Calif.) and includes two struts 22, 24 arranged generally parallel with the direction F of blood flow. In the embodiment of FIGS. 1, 2A, and 2B, the struts 22, 24 are inset to define an annular ledge 26 such that the securing base of the frame 12 has a larger diameter than the struts 22, 24. This arrangement creates sinuses between the leaflets member 14 and the inner walls of the vein 16. The generally tubular leaflets member 14 is wrapped around the outside of the struts 22, 24. In some embodiments, the valve 10 is inserted into the slit 18 with one of the struts 22, 24 aligned with the slit 18. This orientation advantageously covers up the sutured slit 18 by the aligned strut.

In some embodiments, the generally tubular leaflets member 14 is made from a single piece of a non-biological material such as segmented polyurethane (Biospan®, The Polymer Technology Group, Berkeley, Calif.) tubing, which has advantageous fatigue resistance, strength, flexibility, and biocompatibility characteristics. In other embodiments, a biological leaflet material such as small intestine submucosa may be used for the leaflets. In some embodiments, the leaflets member 14 is bonded to the polymer frame 12 using chemical bonding. It is also contemplated to attach the leaflets member in other ways, such as by a frictional fit, a compression fitting, or so forth.

The struts 22, 24 of the polymer frame define gaps 30, 32 (labeled in FIG. 1) therebetween. Valve cusps or leaflets 36, 38 are defined as those portions of the leaflets member 14 disposed at the gaps 30, 32. Because the leaflets member 14 is wrapped around the outside of the struts 22, 24, the valve leaflets 36, 38 tend to stay at or near the perimeter of the vein lumen and therefore do not substantially impede blood flow in the normal direction F. This normally open condition is illustrated in FIG. 2A.

The normal or antegrade venous blood flow in the direction F indicated in FIG. 2A is maintained most of the time. However, in some situations the venous blood flow may have a tendency to temporarily reverse. In major veins of the lower extremities, such a tendency arises when the patient stands up from a sitting position or when the patient engages in certain other rapid movements.

With particular reference to FIG. 2B, the direction of "reverse" or retrograde blood flow is indicated by the back-flow direction B. As the blood flow begins to reverse, the flowing blood tends to draw or collapse the valve leaflets 36, 38 into the gaps 30, 32 between the struts 22, 24, as shown in FIG. 2B. Collapse of the leaflets 36, 38 into the gaps 30, 32 is enhanced by the sinuses formed by the insetting of the struts 22, 24 forming the ledge 26. The collapsed leaflets 36, 38 impede or block backflow of blood in the backflow direction B. In effect, the prosthetic venous valve 10 acts as a "check valve" that allows blood flow only in the normal forward direction F, but not in the backflow direction B. Edges of the valve leaflets 36, 38 are shaped so as to make a complete seal. To ensure good sealing at the edges, the ends of the struts 22, 24 optionally include generally triangular or tapered flanges 40, 42, respectively, each extending in tapered fashion inwardly toward the center of the vein lumen. As best seen in FIG. 2B, the generally tapered flanges 40, 42 help seal against blood backflow in the vicinity where the struts 22, 24 meet the valve leaflets 36, 38.

The closed position of FIG. 2B is not the normal condition of the venous valve 10. Rather, the leaflets member 14 is mechanically biased by its arrangement outside of the struts 22, 24 such that the cusps or leaflets 36, 38 are ordinarily positioned at or near the perimeter of the vein as shown in FIG. 2A. That is, the struts 22, 24 ordinarily bias the leaflets 36, 38 into the open position. Hence, the normally open venous valve 10 presents limited resistance to blood flowing in the normal direction F, and only closes as the blood flow begins to reverse toward the backflow direction B. When the tendency toward backflow is removed, for example after the patient has completed the motion from sitting to standing, the venous blood returns to its normal state of flowing in the normal direction F, and the leaflets 36, 38 return to their unbiased open positions.

In one specific embodiment, the polymer frame 12 has a base diameter of 10 millimeters and the struts 22, 24 are 8 millimeters long in the direction F of normal flow. The 10 millimeter diameter of this embodiment approximately corresponds to the inside diameter of typical superficial femoral veins. In this embodiment, the leaflets member 14 is made from a single piece of segmented polyurethane tubing having a 10 mm diameter and a 0.5 mm thickness, and the valve leaflets 36, 38 are 10 millimeters in length along the flow direction F.

The prosthetic venous valve 10 is readily modified by the skilled artisan to adapt it to specific applications. For example, more than two struts, and hence correspondingly more than two gaps, can be formed. As one example, the prosthetic venous valve 10 can be converted from the illustrated bicuspid valve to a tricuspid valve by including three struts spaced apart at 120° intervals around the vein lumen. It is also contemplated to employ struts which are not exactly aligned with the principal direction F of normal blood flow. Depending upon the material used for the valve frame, it is also contemplated to form the cusps or valving leaflets integrally with the frame, for example by integrally molding a thinned portion in place of the gaps 30, 32 during formation of the polymer frame. Still further, the dimensions of the polymer frame can be varied to suit specific applications and specific materials.

In some embodiments, one or more small openings, such as the optional opening 44, are formed in the leaflets 36, 38. The opening mitigates the effects of the reverse flow associated with a change from a sitting to a standing position. The opening 44 is disposed in the leaflet 38 near a point where the leaflet 38 extends over the gap 32 between the struts 22, 24 such that reverse blood flow is slowed, but not completely stopped, when the blood flow reverses into the reverse or retrograde direction B causing the leaflets 36, 38 to close. The at least one opening 44 is expected to help maintain blood volume while quickly responding to abrupt flow direction changes, to reduce pressure shock to the valve leaflets while minimizing blood pooling in the extremities.

With reference to FIG. 3, as an example of such a variation, a polymer frame 12' is similar to the polymer frame 12 of FIG. 1, and includes a suture fastening groove 20' similar to the groove 20 of the frame 12. However, the frame 12' has struts 22', 24' that are wider than the struts 22, 24 of the frame 12. The wider struts 22', 24' may be advantageous, for example, if the leaflets are made of a more flexible material that requires additional support to be maintained in the normally open position. The struts 22', 24' include optional tapered flanges 40', 42', respectively, which are similar to the tapered flanges 40, 42 of the struts 22, 24 of the polymer frame 10. Moreover, the struts 22', 24' are inset on the frame to define an annular ledge 26' similar to the annular ledge 26 of the frame 12.

With reference to FIGS. 4, 5A, and 5B, in another embodiment a normally open prosthetic venous valve 50 includes a generally hollow wire frame 52, surrounded by a flexible generally tubular leaflets member 54. The prosthetic venous valve 50 is implanted into a vein 56 (shown in phantom). When implanted, the wire frame 52 is arranged coaxially with the vein 56, and the generally tubular leaflets member 54 is arranged coaxially with the vein on the outside of the generally hollow wire frame 52, so that the prosthetic venous valve 50 does not substantially impede venous blood flowing in the normal direction F.

The prosthetic venous valve 50 is secured inside the vein 56 by retention hooks (not shown) or other fasteners, or by an adhesive, friction fit, compression fit, or so forth. The frame 52 includes a wire base 60 defined by a short circular wire frame portion and includes two wire struts 62, 64 arranged generally parallel with the direction F of blood flow. The wire struts 62, 64 are defined in the illustrated frame 52 by elongated wire loops. The struts 62, 64 are widest where they join the wire base 60, and taper to a narrower width at the end distal from the wire base 60. The generally tubular leaflets member 54 is wrapped around the outside of the struts 62, 64. The leaflets member 54 is attached to the wire frame 52 by molding it around the struts 62, 64, or by using an adhesive, friction fit, compression fit, or so forth. In some embodiments, the leaflets member 54 is suitably made Biospan® tubing.

The wire struts 62, 64 of the wire frame 52 define gaps 70, 72 (labeled in FIG. 4) therebetween. Valve cusps or leaflets 76, 78 are defined as those portions of the leaflets member 54 disposed at the gaps 70, 72. Because the leaflets member 54 is wrapped around the outside of the wire struts 62, 64, the valve leaflets 76, 78 tend to stay at or near the perimeter of the vein lumen and therefore do not substantially impede blood flow in the normal direction F. This normally open condition is illustrated in FIG. 5A.

With particular reference to FIG. 5B, when the blood flow begins to reverse toward the backflow direction B, the flowing blood tends to draw or collapse the valve leaflets 76, 78 into the gaps 70, 72 between the wire struts 62, 64, as shown in FIG. 5B. The collapsed leaflets 76, 78 impede or block backflow of blood in the backflow direction B. In effect, the prosthetic venous valve 50 acts as a "check valve" that allows blood flow only in the normal forward direction F, but not in the backflow direction B. The leaflets member 54 extends in the flow direction F beyond the ends of the wire struts 62, 64, and the portion extending beyond the ends of the struts includes cuts or slits 80, 82 aligned with the struts to allow less constrained movement of the ends of the leaflets 76, 78 when they collapse together under flow in backflow direction B. To ensure substantially complete closure, the edges of the slits 80, 82 and the edges of the leaflets 76, 78 are shaped into an arc length corresponding to a diameter defined by a separation of the wire struts 62, 64.

The closed position of FIG. 5B is not the normal condition of the venous valve 50. Rather, the leaflets member 54 is mechanically biased by its arrangement outside of the wire struts 62, 64 such that the cusps or leaflets 76, 78 are ordinarily positioned at or near the perimeter of the vein as shown in FIG. 5A. That is, the wire struts 62, 64 ordinarily bias the leaflets 76, 78 into the normal open position. Hence, the venous valve 50 presents limited resistance to blood flowing in the normal direction F, and only closes upon reversal of blood flow into the reverse direction B. When the tendency toward backflow is removed, for example after the patient has completed the motion from sitting to standing, the venous blood returns to its normal state of flowing in the normal direction F, and the leaflets 76, 78 return to their unbiased open positions.

In some embodiments, it is contemplated to insert the venous valve 50 into a vein using a catheter. In such an approach, the wire base 60 is compressed by the catheter tip mechanism prior to insertion into the vein. The catheter is used to position the venous valve 50 into place, and then the catheter tip releases the base compression so that the wire base 60 expands to contribute to securing the venous valve 50 inside the vein. Expansion of the wire base 60 leads to an enlarged diameter of the base cross-section and the formation of sinuses outside the leaflets 76, 78. These sinuses are contemplated to improve valve closure by providing an increased contact area for blood beginning to reverse flow toward the backflow direction B to interact with the leaflets 76, 78 and bias the leaflets 76, 78 into the vein lumen.

In one specific embodiment, the wire base 60 has a diameter of 10 millimeters and the struts 22, 24 are 5 millimeters long in the direction F of normal flow, and taper from a width of 3 millimeters where the struts 22, 24 join the base 60 to a width of 1.5 millimeters at the tips of the struts 22, 24. Metallic hooks (not shown) at the proximal and distal ends of the struts 22, 24 securely attach the frame 52 to the vein 56. In this embodiment, the leaflets member 54 is made from a single piece of segmented polyurethane tubing having a 10 mm diameter and a 0.5 mm thickness, and the slits 80, 82 provide 3 millimeters of movement at the ends of the valve leaflets 76, 78. The slits 80, 82 and the edges of the leaflets 76, 78 in this embodiment are tapered inward by 2.85 millimeters to facilitate substantially complete valve closure.

The prosthetic venous valve 50 is readily modified by the skilled artisan to adapt it to specific applications. For example, the valve can be modified to form a tricuspid valve by including three wire loop struts spaced apart at 120° intervals around the wire base. It is also contemplated to tilt the wire struts respective to the base so that they are not exactly aligned with the principal direction F of normal blood flow.

With reference to FIGS. 6A, 6B, and 6C, another polymer frame 112 is similar to the polymer frame 12 of FIGS. 1, 2A, and 2B, and includes a suturing groove 120 and struts 122, 124 corresponding to the groove 20 and struts 22, 24, respectively, of the frame 12. The frame 112 differs from the frame 12 in two principal respects. First, the struts 122, 124 are not inset relative to the annular base of the frame 112; accordingly, the ledge. 26 of the frame 12 has no analog in the frame 112. Second, the struts 122, 124 do not have the inwardly extending flanges 40, 42 of the struts 22, 24. As best seen in the top view of FIG. 6B, these differences result in the polymer frame 112 introducing a very limited stenosis to the vein. That is, the opening of the valve 112 through which venous blood flows is substantially unrestricted. Elimination of the ledge 26 reduces the sinuses between the leaflets and the vein walls; however, mechanical coupling to effect closure of the leaflets during reversal of venous blood flow can be achieved in other ways, such as by tapering or otherwise shaping the edges of the leaflets.

With reference to FIGS. 7A, 7B, and 7C, another polymer frame 212 is similar to the polymer frame 112 of FIGS. 6A, 6B, and 6C, and includes a suturing groove 220 and struts 222, 224 corresponding to the groove 120 and struts 122, 124, respectively, of the frame 112. The frame 212 differs from the frame 112 in that the struts 222, 224 are triangular in shape and come to sharp points. The shape of the polymer frame 212 is also expected to be suitable for wire frames similar to the wire frame 52 of FIG. 4; however, when the shape of the frame 212 is formed by a wire frame, the suturing groove 220 is suitably omitted and hooks or other fasteners are suitably used to secure the wire frame inside the vein.

With reference to FIGS. 8A, 8B, 8C, and 8D, another polymer frame 312 is similar to the polymer frame 12 of FIGS. 1, 2A, and 2B, and includes a suturing groove 320 and struts 322, 324 corresponding to the groove 20 and struts 22, 24, respectively, of the frame 12. The frame 312 differs from the frame 12 in two principal respects. First, the struts 322, 324 are not inset relative to the annular base of the frame 112; accordingly, the ledge 26 of the frame 12 has no analog in the frame 112. (Thus, the frame 312 is similar to the frames 112, 212 in this respect of omitting the ledge 26). Second, the struts 322, 324 have larger and differently shaped inwardly extending flanges 340, 342 versus the struts 22, 24. The increased stenosis produced by the larger flanges 340, 342 is at least partially balanced by reduction in stenosis produced by omitting the ledge 26 of the valve frame 12.

The valve flanges 340, 342 are mathematically engineered to provide a close match between the amount of leaflet material present in the open position and the amount of leaflet material available to close around the struts 22, 24 and span the orifice in the closed position. This close match limits formation of buckles, pleats, or the like in the closed position, thus reducing or eliminating gaps between the leaflet edges that could lead to valve incompetence. The flanges 340, 342 also have substantially constant radii of curvature such that, upon closure, each valve leaflet will flex to a similar degree along its entire length of contact with the flanges 340, 342 to avoid generating areas of high compressive or tensile stress. It is expected that the more uniform stressing of the leaflets should increase the number of repeating operating cycles before occurrence of fatigue failure.

Longitudinally, the valve flanges 340, 342 are gradually tapered up and back down in the longitudinal flow direction so that no abrupt edges or transitions are present. This shape reduces areas of flow stagnation and flow separation as the blood enters and leaves the valve frame 312. The improved axial or z-directional (referencing the coordinate system of FIG. 12B) blood flow is expected to reduce the incidence of stasis-induced thrombosis, induce a stabilizing effect on the blood, and minimize any traumatic effects on the blood due to secondary motions.

With reference to FIGS. 9A, 9B, and 9C, another polymer frame 412 is similar to the polymer frame 312 of FIGS. 8A, 8B, 8C, and 8D, and includes a suturing groove 420 and struts 422, 424 corresponding to the groove 320 and struts 322, 324, respectively, of the frame 312. The struts 422, 424 include shaped flanges 440, 442 similar to the flanges 340, 342 of the struts 322, 324, but with an improved shape. As in the frame 312, the frame 412 omits the ledge 26 of the frame 12. The frame 412 differs from the frame 312 in that the base of the frame 412 is elliptical, whereas the base of the frame 312 is circular. As best seen in FIG. 9A, the long axis of the elliptical base is transverse to a line connecting the struts 422, 424. That is, a diameter of the elliptical base between the struts 422, 424 is smaller than a diameter of the elliptical base in the transverse direction.

The purpose of the elliptical base of the frame 412 is to induce a distention of the vein wall behind the free edges of the valve leaflets which will create a flow vortex. In cardiac aortic, mitral, and other cardiac valves, such flow vortices behind the valve leaflets have been found to enhance valve closure prior to cessation of forward flow and, thus, provide extremely low amounts of flow regurgitation. In effect, the elliptical base of the frame 412 is expected to produce slightly larger sinuses between the leaflets and the vein walls. Mechanical coupling between reversing venous blood flow and the leaflets is enhanced by the slightly larger sinuses generated by the elliptical base, thus promoting faster valve closure during reversal of venous blood flow.

With reference to FIGS. 10, 11A and 11B, 12A and 12B, 13, 14A and 14B, 15, 16, and 17A and 17B, several valves incorporating various features disclosed herein were constructed at about a 1:1 scale and tested in a horizontal pulsatile flow system.

Figure 11A:
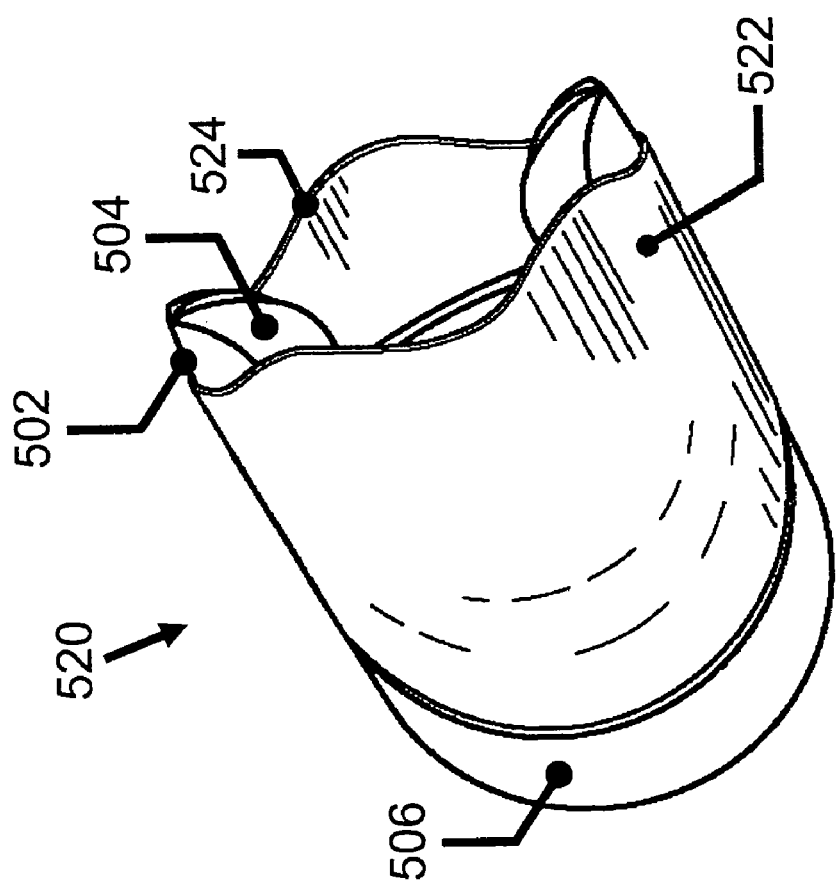

FIGS. 10, 11A and 11B, and 12A, 12B, and 12C show a first type of 1:1 scale venous valve tested. This valve type includes a frame 500 with struts 502 having flanges 504 shaped similarly to the strut flanges 340, 342, 440, 442 of the frames 312, 412 previously described, and includes a base 506 and suture ring 508 for securing into a vein by a suture loop. The struts 502 of the frame 500 include shoulders 510 defined by a cross-section of the strut 502 that narrows in the direction away from the base 506. The frame 500 also includes a beveled connecting surface or surfaces 512 disposed between outer and inner principal surfaces of the frame 500. The beveled connecting surface 512 is disposed on the shoulders 510 and in the region between the shoulders 510. The shoulders 510 refer to the supporting structure between the flange 504 and the edge of the base 506 proximal to the x-y plane of the origin. The beveled connecting surface 512 defines an inward tapering of the frame 500 in the general direction from the inflow end to the outflow end of the valve. The complete valve 520 including the frame 500 and coaxially attached generally tubular leaflets member 522 is shown in FIG. 11A (normal open valve position) and in FIG. 11B (closed valve position). Optionally, the portion of the beveled connecting surface 512 along the base edge includes an adhesive (not shown) to secure the leaflets, which may produce improved formation of sinus regions for facilitating valve closure. In some embodiments, the leaflets have curved free edges selected such that a path length of the closed leaflet around one of the struts 502 is matched to that of the fully open leaflet having a circular cross-section of radius R. In prototypes of the first type, the shape of each flange 504 was selected to be semi-circular continuing into an inverted quarter-circle. The path-length around one side of the frame to the center of the tube was selected to be equal to the quarter circumference of the tube. Accordingly, a value for the minor radius, r (see FIG. 12A), was obtained as:

$$r = \frac{\pi}{4+3\pi} \cdot R \cong 0.234 \cdot R. \qquad (1)$$

This design allows for complete closure of the leaflets defined between the struts 502 by the generally tubular leaflets member 522 while also imposing a constant radius of curvature, and thus, constant bending stresses on the leaflet at all points.

In prototype valves of the first type, the frame was further defined in the axial direction by tapering the flange 504 gradually up to this shape from the circular base 506 and then back down at the outflow end. A final consideration was made of the shape of the generally tubular leaflets member 522 in the axial direction because of the natural tendency of the leaflets to close at a lower point in the center of the tube than around the frame 500. Thus, a generally tubular leaflets member of uniform axial height would intersect its mating piece along an oblique, rather than cross-sectional, plane and not conform to the optimized path. To address this concern, contacting edges or commissures 524 the generally tubular leaflets member 522 were shaped to lie along a single, cross-sectional plane 526 in the closed position shown in FIG. 12B. Accordingly, the generally tubular leaflets member 522 was cut to define the contacting edges or commissures 524 defined by a curved free edge based upon geometric considerations.

Figure 12A:
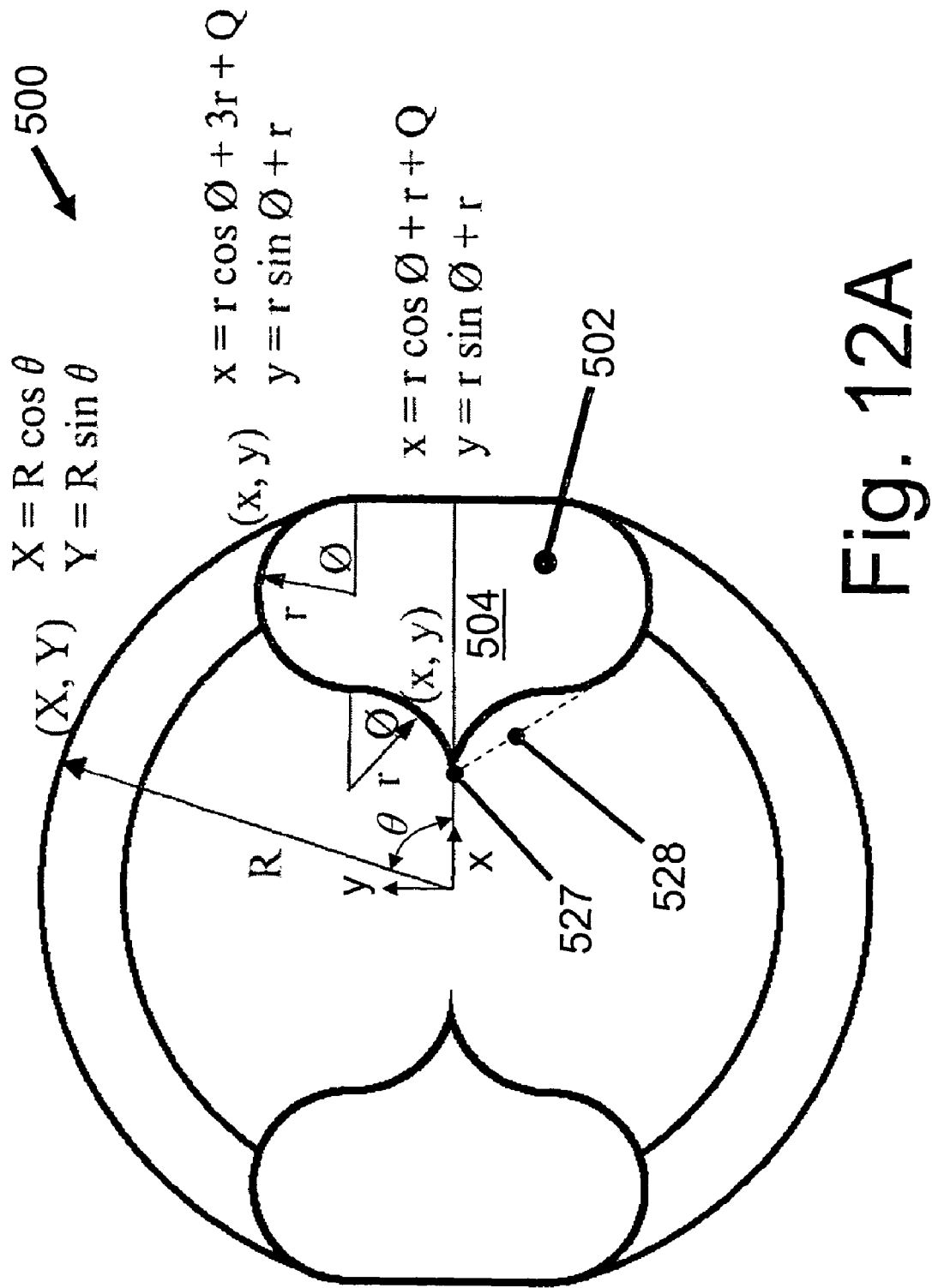
FIGS. 12A and 12B show apex-end and side views, respectively, of the valve frame of FIG. 10, including dimensions used in the design.

With brief reference to FIG. 12A, the illustrated flange 504 of prototype prosthetic valves of the first type was selected to be semi-circular continuing into an inverted quarter-circle that produces a relatively sharp tip 527 to the flange. This arrangement is suitable for thin leaflets, so as to suppress leakage at the leaflet/flange junction when the valve is closed. However, for thicker leaflets, a flattened inner edge 528 (indicated in FIG. 12A by a dashed line) of the flange 504 is contemplated. The flattened inner edge 528 is expected to be more readily manufactured, more resistant to breakage, and, for thicker leaflets, is expected to provide good sealing at the leaflet/flange junction.

The leaflets 522 were designed to limit potential thrombogenicity of the valve 520 by reduced leaflet area. Having a closure along the midplane 526 of the flange also reduces the frame surface area and thus further reduces potential thrombogenicity. The angle of leaflet flexion at the proximal edge of the base, which is a high stress region was also considered. Decreasing the angle of leaflet closure decreases stress, but calls for lengthening the flange which increases leaflet surface area. The leaflets 522 were also designed to have sufficient pre-closing area in the flow stream for a reversing pressure to act upon and initiate closure when needed.

Figure 12B:
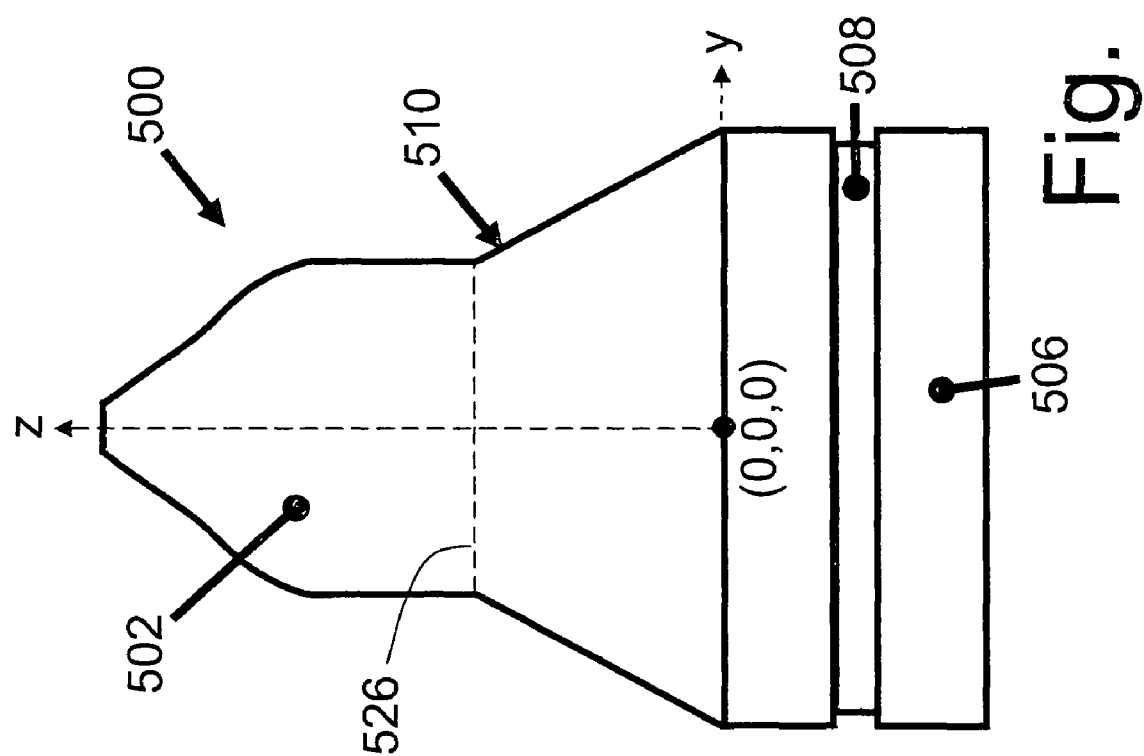
Figure 12C:
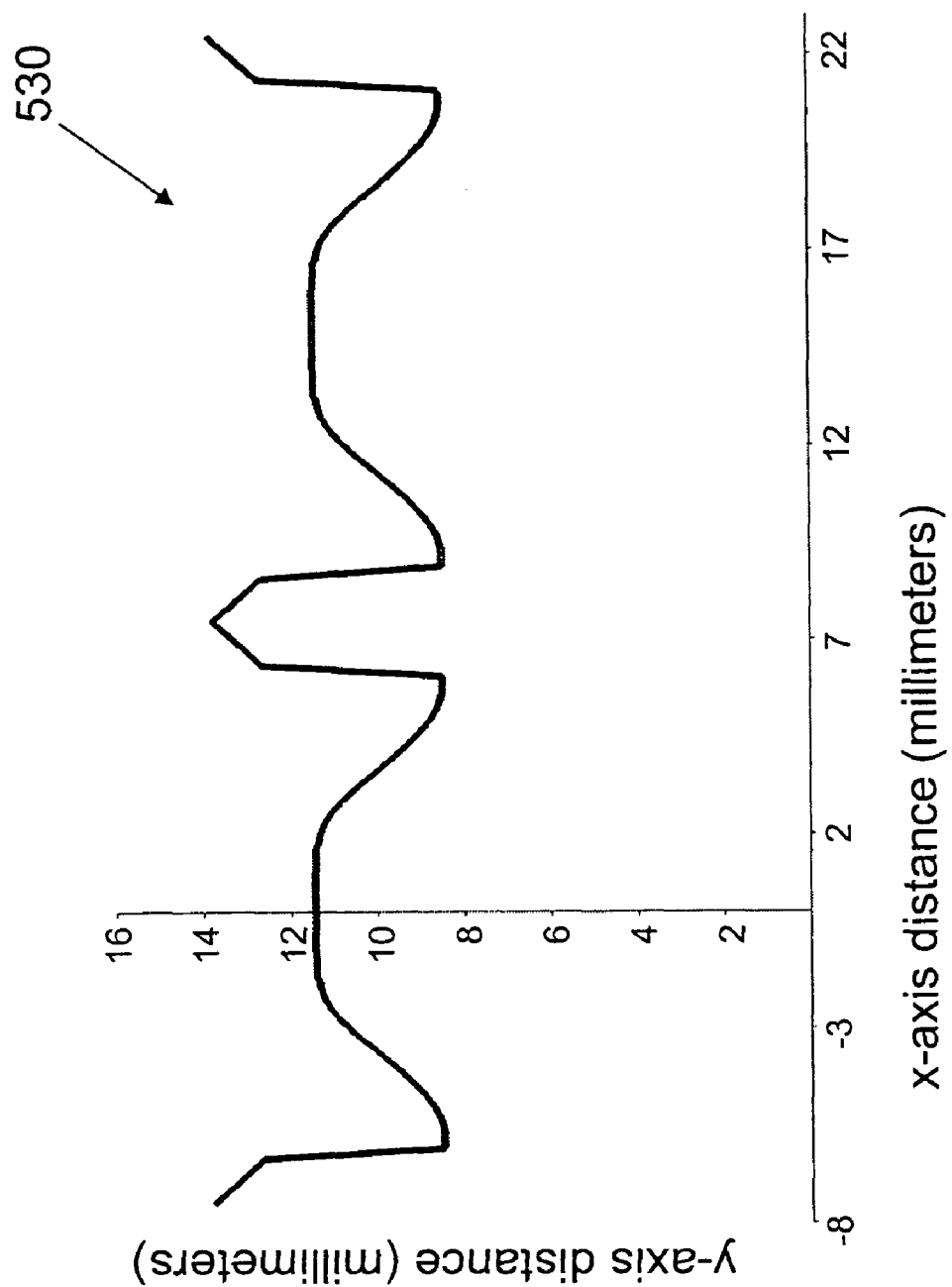
FIG. 12C shows a suitable template for cutting the leaflets.
Figure 13:
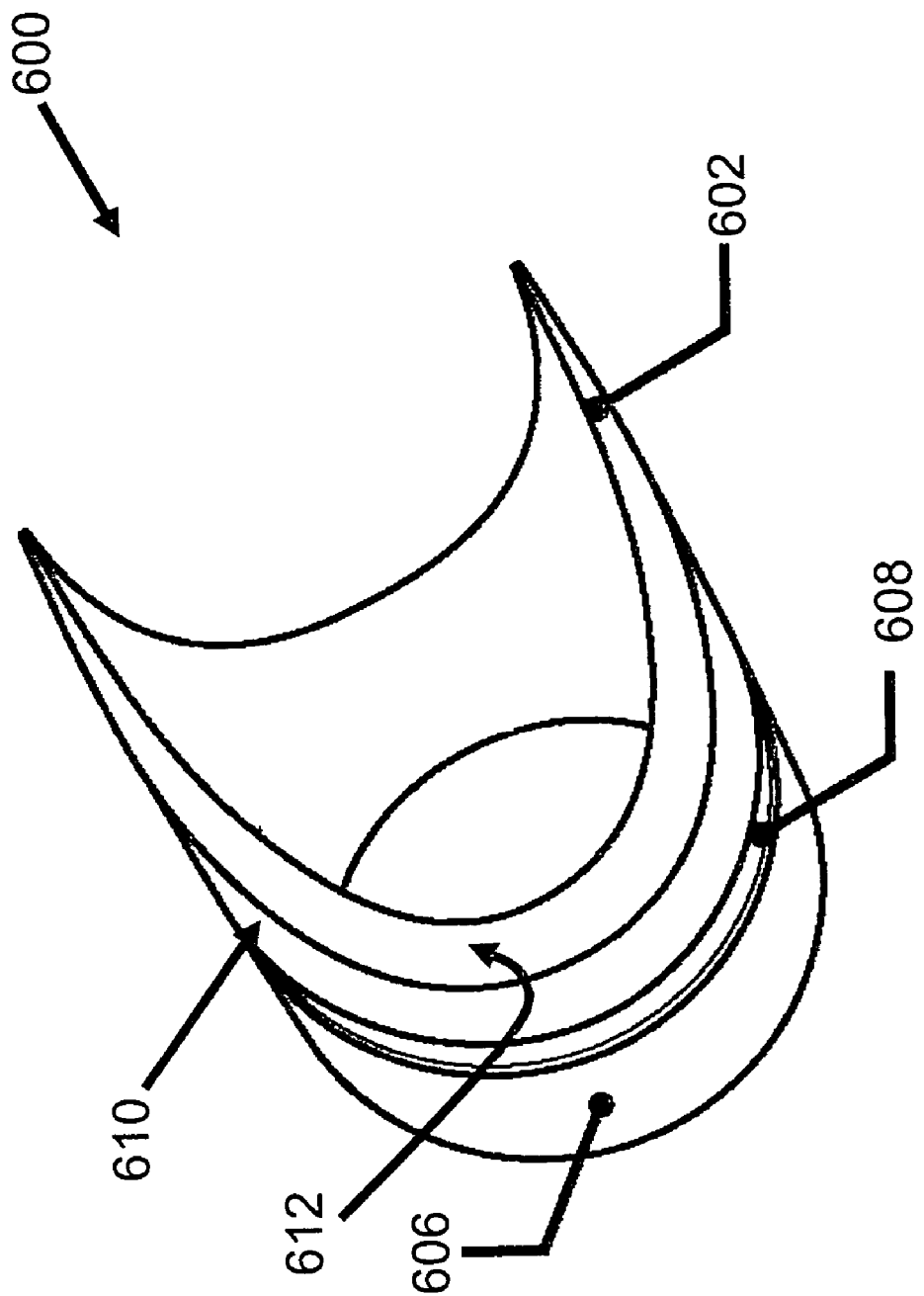
FIG. 13 shows a perspective view of a frame of a second prototype valve type design.

With particular reference to FIGS. 12A, 12B, and 12C, a suitable example approach for determining the shape of the flanges 504 and leaflets 522, which was used in designing the prototype test frames of the first type, is described. The plane 526 was defined along the untapered flange where the proximal edges of the leaflets meet when in the closed position. This plane 526 was parallel to the circumferential plane and was defined to be at the axial midpoint of the fully developed flange 504. This provided a safety factor in that if there were errors in the leaflet meeting in the closure plane then it would still close on a portion of the untapered flange and thus, continue to provide a substantially complete seal upon flow reversal. A three-dimensional Cartesian (x,y,z) coordinate system was designated, with the x-y plane being parallel to the circumferential plane of the frame 500, the x-axis directed towards the back of the flange 504, and the y-axis pointed towards the valve sinus. The z-axis was perpendicular to the x-y plane and followed the axis of the valve lumen. The point (0,0,0) of the Cartesian coordinate system was designated to be on the valve axis in the x-y plane and at the proximal base edge in the y-z or x-z-planes.

With particular reference to FIG. 12A which views the frame in the x-y plane, points from the radial edge of the base 506 were mapped to their corresponding points on the flange 504 during full closure using a spreadsheet program (Microsoft Excel, Microsoft Corporation, Redmond, Wash.). In two-dimensions, the distance between these points was the minimum leaflet length to ensure full closure. This was done by defining an offset angle $\theta_{off}$ as the angle formed by the x-axis and the point on the flange back that protruded furthest in the y-direction. Along the back of the flange 504, all points of the base 506 and flange 504 were identical and therefore, the $\theta_{off}$ variable excluded these points from the calculation. For the frame 500, $\theta_{off}=12.69°$. The x-y coordinates of all the points on the radial edge of the base 506 were determined by incrementing the angle from the x-axis by 0.25 radians and applying the following equations:

$$X = R \cos \theta \qquad (2),$$

and $$Y = R \sin \theta \qquad (3),$$

where X denotes the Cartesian coordinate of the radial base edge from the x-axis, Y denotes the Cartesian coordinate of the radial base edge from the y-axis, R denotes the valve radius, and $\theta$ denotes the angle from $\theta_{off}$ in radians. The points on the radial base edge were mapped to their corresponding points on the flange 504 using the following relationship for the arc length (denoted s):

$$s = R\theta = r\phi \qquad (4),$$

where r denotes the radius of the flange 504 and $\phi$ denotes the angle of the flange 504 from $\theta_{off}$. For the frame 500, R was set at 6.25 millimeters, and the corresponding value for r was 1.37 millimeters. Because $\theta$ was incremented, $\phi$ became the dependent variable. Physically, $\phi$ was the angle formed by the $\theta_{off}$ reference point on the base and a specific point on the flange 504. Analogous to the X,Y coordinate system on the radial base edge, two-dimensional Cartesian coordinate positions of the flange surface were determined from the following equations:

$$x = r \cos \phi + x' \qquad (5),$$

and $$y = r \sin \phi + y' \qquad (6),$$

where x denotes the Cartesian coordinate of the flange 504 from the x-axis, y denotes the Cartesian coordinate of the flange 504 from the y-axis, r denotes the radius of the flange 504, $\phi$ denotes the angle from $\theta_{off}$ of the flange in radians, x'=x offset, and y'=y offset, all relative to the origin (0,0,0). The offsets, x' and y', were employed because the points of the flange 504 were based on circles that had different centers. Thus, for the portion of the flange 504 composed of the half-circle, x' equaled (Q+3r) and for the frame 500 was 4.71 millimeters. Similarly, y' was r or 1.37 millimeters. For the quarter-circle portion, x' was (Q+r) or 1.97 millimeters and y' was r or 1.37 millimeters. The line connecting the tip of the flange 504 and the origin was linear and therefore, a separate mathematical definition was used for mapping the remaining arc length of the radial base edge. These points were evenly distributed along the remainder of the closure path. To resolve the coordinates of the third dimension, the frame was viewed in the y-z plane (see FIG. 12B) and the displacement in the z-direction determined. For the radial base edge, the z-coordinate is zero and, similarly, the z-coordinates of the closure plane all have a constant value. These relationships are suitably expressed as:

$$Z = 0 \qquad (7),$$

and $$z = n \qquad (8),$$

where Z denotes the Cartesian coordinate of the radial base edge from the z-axis, z denotes the Cartesian coordinate of the flange from the z-axis, and, n denotes the predetermined leaflet closure height. The minimum leaflet length for ensuring full closure at the flange midplane 526 was calculated as the three-dimensional resultant of the leaflet attachment point on the radial base edge to its corresponding mapped point in the closure plane. This was done using the following relationship:

$$L = \sqrt{(X-x)^2 + (Y-y)^2 + (Z-z)^2} \qquad (9),$$

where L denotes the minimum length of the leaflet for full closure. The valve base height was added to L and provided an overlap between frame and leaflet material for the application of adhesive, coaxial frictional fit, or other securing. Tabulation of L versus $\theta$ provided a series of data points that when plotted against the values of X created one-quarter of a two-dimensional leaflet template. Utilizing symmetry and additions for the flange back, a template 530 (shown in FIG. 12C) was produced that was used to form the leaflet 522 when cut out of material and wrapped around the valve frame 500.

Figure 14A:
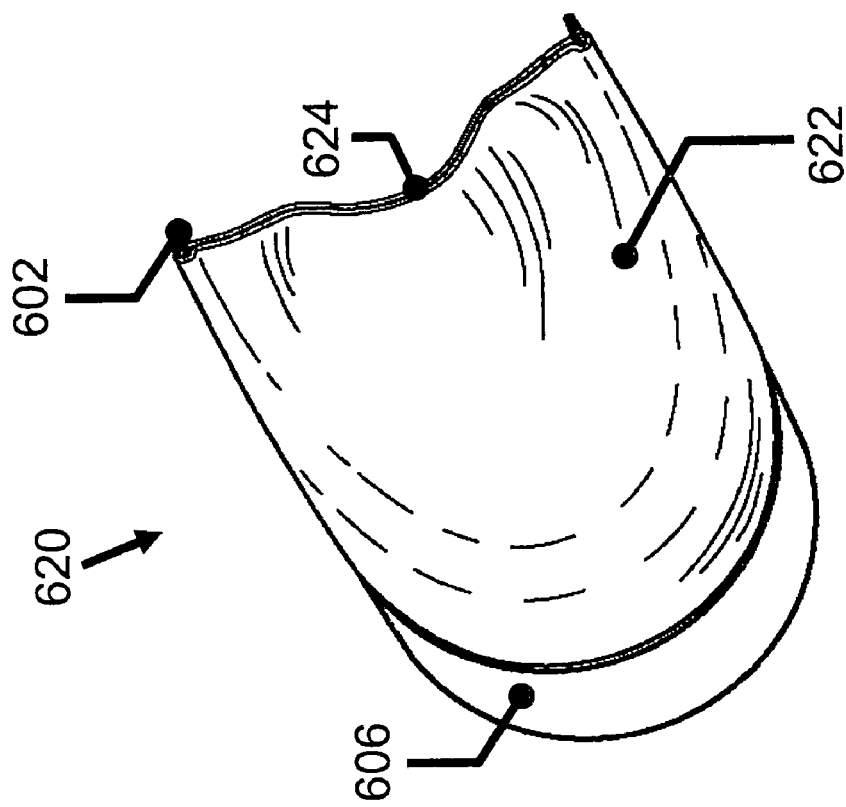
FIGS. 14A and 14B show perspective views of the second prototype valve type including the frame of FIG. 13 and a generally tubular leaflets member in the open and closed positions, respectively.
Figure 14B:
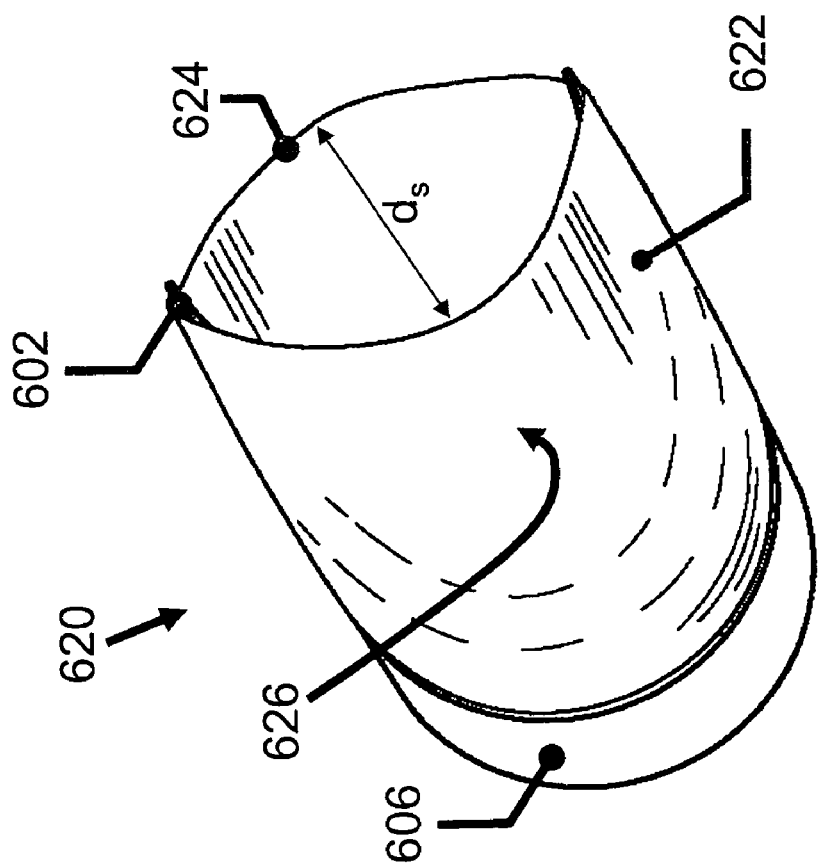
Figure 15B:
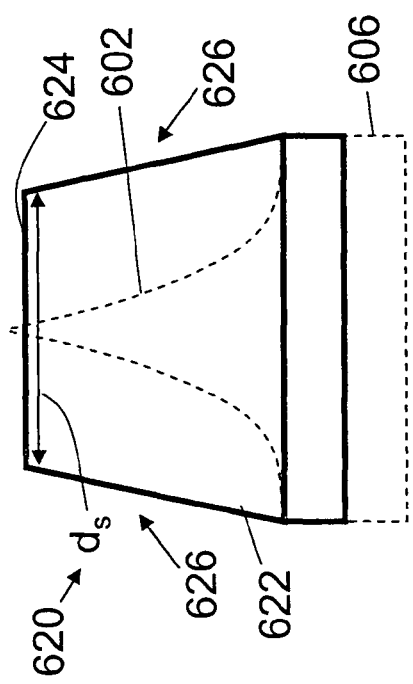
FIGS. 15A, 15B, and 15C show apex-end, and two 90° rotated perspective side views, respectively, of the valve of FIGS. 14A and 14B in its normally open position. In these FIGURES, the frame of FIG. 13 is drawn with dashed lines while the generally tubular leaflets member is drawn with solid lines.
Figure 15C:
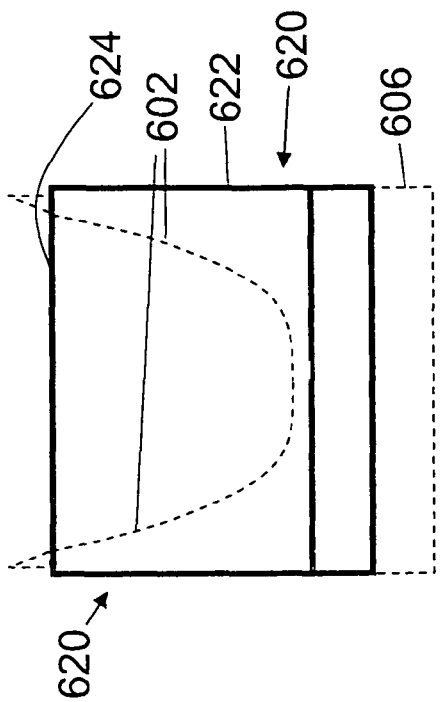
Figure 15A:
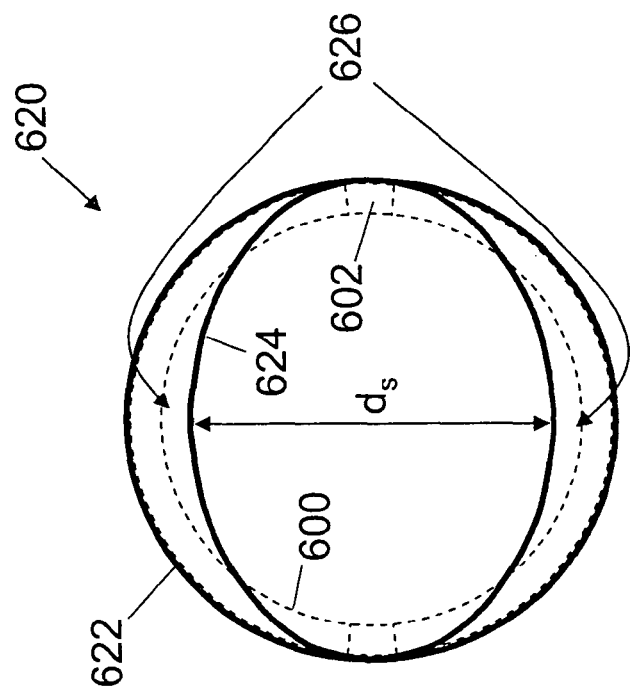

FIGS. 13, 14A and 14B, and 15A, 15B, and 15C show a second type of 1:1 scale venous valve tested. This valve type includes a frame 600 with struts 602 that are tapered to a sharp or blunted tip similarly to the struts 222, 224 of the frame 212 previously described, and includes a base 606 and suture ring 608 for securing into a vein by a suture loop. The struts 602 of the frame 600 include a shoulder 610 defined by a cross-section of the strut 602 that narrows in the direction away from the base 606. The frame 600 also includes a beveled connecting surface or surfaces 612 disposed between outer and inner principal surfaces of the frame 600. The beveled connecting surface 612 is disposed on the shoulders 610 and in the region between the shoulders 610. The beveled connecting surface 612 defines an inward tapering of the frame 600 in the general direction from the inflow end to the outflow end of the valve. The complete valve 620 including the frame 600 and coaxially attached generally tubular leaflets member 622 is shown in FIG. 14A (normal open valve position) and in FIG. 14B (closed valve position). In the prototype valves of the second type, the frame 600 was designed to fully support the generally tubular leaflets member 622. The height of the struts 602 was selected to equal the diameter of the venous vessel, and the struts 602 were narrowed in a logarithmic manner toward their apex ending in a blunted tip to define the shoulders 610. The shoulders 610 are believed to act in conjunction with the beveled connecting surfaces 612 to help define valve sinuses between the leaflets between the struts 602 formed by the generally tubular leaflets member 622 and the venous vessel wall for facilitating closing of the valve 620 from its normally open position. The leaflets defined by the generally tubular leaflets member 622 extend from the base 606 to the tip of the strut 602 and may have either a straight or semi-circular shape at their apexes. In the prototype valves of the second type, the generally tubular leaflets member 622 was created from a tubular piece of polymer positioned to surround the struts 602. The diameter of the base of the generally tubular leaflets member 622 was selected to match the diameter of the frame base 606, and the diameter at the outflow end was selected in various prototypes to narrow at the outflow end to between about 70% and about 95% of the base diameter. The generally tubular leaflets member 622 had the shape of a frustum of a cone prior to being placed over the frame 600. An outflow leaflets diameter of between about 70% and about 85% of the base leaflets diameter was found to be effective for enhancing spontaneous closure responsive to flow reversal without producing problematic stenosis. As best seen in FIGS. 15A, 15B, and 15C which show apex-end view and two 90° rotated perspective side views, respectively, of the valve 620 in its normally open position, after coaxial placement of the tapered generally tubular leaflets member 622 over the frame 602 the apex end of the generally tubular leaflets member 622 conformed with the diameter of the frame 600 at the overlap with the struts 602, and was narrowed along contacting edges or commissures 624 to a smaller diameter $d_s$ along the diameter transverse to the struts (see FIGS. 15A and 15B), thus defining valve sinuses 626. This geometry produces leaflets that lie along the inner vein wall during forward flow of blood but are canted slightly inward to form sinuses that facilitate rapid valve closure responsive to blood backflow.

Figure 16:
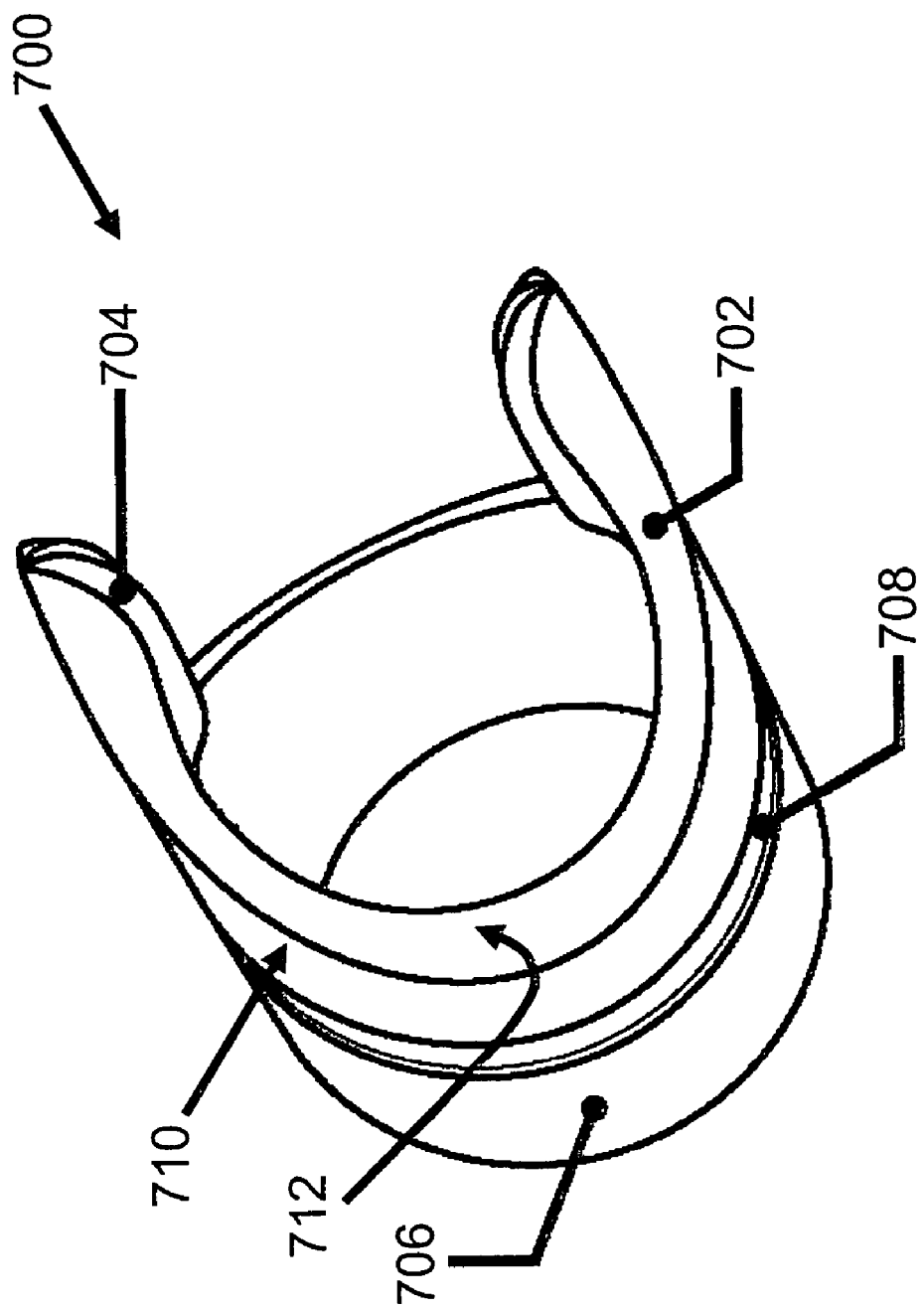
FIG. 16 shows a perspective view of a frame of a third prototype valve type design.

FIGS. 16 and 17A and 17B show a third type of 1:1 scale venous valve tested. This valve type includes a frame 700 with struts 702 having flanges 704 shaped similarly to the strut flanges 340, 342, 440, 442 of the frames 312, 412 previously described. The flanges 704 are reduced in size by about 15% (that is, the radii r are reduce by about 15%) compared with the flanges 504 of the first valve type 520. The frame 700 further includes a base 706 and suture ring 708 for securing into a vein by a suture loop. The struts 702 of the frame 700 include a shoulder 710 defined by a cross-section of the strut 702 that narrows in the direction away from the base 706. The frame 700 also includes a beveled connecting surface or surfaces 712 disposed between outer and inner principal surfaces of the frame 700. The beveled connecting surface 712 is disposed on the shoulders 710 and in the region between the shoulders 710. The beveled connecting surface 712 defines an inward tapering of the frame 700 in the general direction from the inflow end to the outflow end of the valve. The complete valve 720 including the frame 700 and coaxially attached generally tubular leaflets member 722 is shown in FIG. 12A (normal open valve position) and in FIG. 12B (closed valve position). The frame 700 is designed to support a generally tubular leaflets member 722 with a circular apex end defining contacting edges or commissures 624.

In the valves 520, 620, 720, the beveled connecting surfaces 512, 612, 712 define an inward tapering of the frame in the general direction from the inflow end to the outflow end of the respective valve 520, 620, 720. The valve leaflets drape across the beveled connecting surfaces during valve closure. The beveled connecting surfaces are expected to provide a degree of in-folding of the valve leaflets so as to promote rapid spontaneous leaflet closure upon blood flow reversal. The beveled connecting surfaces 512, 612, 712 define an inward tapering of the frame in the general direction from a blood inflow end to a blood outflow end of the prosthetic venous valve that enables the leaflets to fold inward slightly. Thus, the leaflets lie along the inner vein wall during forward flow of blood, but are canted slightly inward by the beveled connecting surfaces 512, 612, 712 to define sinuses between the leaflets and the inner vein wall that promote rapid closure of the leaflets to block backflow of blood. The canting of the leaflets is also supported in conjunction with the beveled surfaces 512, 612, 712 by the shoulders 510, 610, 710. The beveled surfaces 512, 612, 712 and shoulders 510, 610, 710 are also expected to inhibit prolapse of the leaflets under high back-flow conditions. The shoulders 510, 610, 710 also enhance the strength of respective struts 502, 602, 702.

An inward tapering of the generally tubular leaflets members from the inflow end to the outflow end of the valve can be provided to promote formation of sinuses between the leaflets and the inner vein wall to promote rapid closure of the leaflets to block backflow of blood. Thus, the leaflets lie along the inner vein wall during forward flow of blood, but are canted slightly inward by the inward tapering of the generally tubular leaflets member. A large inward tapering can be problematic, because the narrowed diameter of the leaflets member at the outflow end caused by large inward tapering is expected to produce substantial stenosis. A tapering such that the outflow end diameter of the generally tubular leaflets members 522, 622, 722 is about 70-85% of the inflow end diameter of the generally tubular leaflets members 522, 622, 722 has been found to provide substantially enhanced valve closure without introducing problematic stenosis. In some of the 1:1 scale prototype valves of the second and third types that have been tested, the generally tubular leaflets members 622, 722 have included inward tapering such that the outflow end has a diameter of between 70% and 95% of the inflow end diameter. In the tested 1:1 scale prototype valves, the taper was generally linear from the inflow end to the outflow end, such that the tapered generally tubular leaflets member had the shape of a frustum of a cone prior to distortion when coaxially placed over the valve frame. However, it is contemplated to use non-linear tapers or to taper the leaflet member along only an axial portion. For example, it is contemplated to taper the leaflet member only near the outflow end so as to provide a canted surface to facilitate valve closure.

In some embodiments, the beveled connecting surfaces 512, 612, 712 are used alone to provide closure-enhancing sinuses. In some embodiments, the inward tapering of the generally tubular leaflets members is used alone to provide closure-enhancing sinuses. In some embodiments, both the beveled connecting surfaces and the inward tapering of the generally tubular leaflets members are used together to provide closure-enhancing sinuses.

Fifteen different prototype valves of the types 520, 620, 720 were constructed by a stereolithography technique at a 1:1 scale (outer diameter=12.5 millimeters) respective to natural veins. Each of the fifteen prototype valves included the beveled connecting surfaces, since previous simulations on 2:1 scale prototype valves had indicated substantial advantages of the beveled connecting surfaces. One prototype prosthetic valve was also constructed with a wire frame similar to that of FIG. 4. Fifteen of the 1:1 scale prototype valves used 5 mil (127 micron) thick BioSpan® leaflets. One of the 1:1 scale prototype valves of the third type 720 used small cut pieces of SIS-OASIS™ small intestine submucosa wound dressing (available from Cook Biotech Incorporated, West Lafayette, Ind.) for the leaflets. The leaflet members of some of the prototype valves of the second and third types 620, 720 included tapering. The leaflet members of the prototype valves of the first type 520 were not tapered, but included the curved free edges 524 at the outflow end designed as described previously herein to reduce regurgitation in the closed position.

The 1:1 scale valves were tested in the horizontal pulsatile flow system. The tests indicated that the valves in the open position introduced effective stenoses of less than 15.5% based on measured effective orifice area values of the tested valves. Average pressure drop across the valve in the open position was less than about 3.0 mmHg for the tested valves. The forward resistance of the valve in the open position was less than about 2.3 mmHg·min/L for the tested valves. In the closed position, valves of the valve type 520, 720 provided better performance than valves of the valve type 620. Some valves of types 520, 720 exhibited less than 5% regurgitation in the closed position with 42.3 mmHg of applied fluid back-pressure. Valves of the second valve type 620 exhibited higher regurgitation. It is believed that the relatively poorer performance of the prototype valves of the valve type 620 was due at least in part to poor closure of the relatively thick 5 mil (127 micron) thick BioSpan® leaflets. Better performance for valve type 620 is expected to be achievable by using thinner BioSpan® leaflets or leaflets of another, more flexible material.

The illustrated embodiments employ generally tubular leaflets members 14, 54. However, in some other contemplated embodiments, the leaflet member includes separate leaflets each secured to the frame in a gap between two neighboring struts. In some embodiments, the frame and/or leaflets member of the prosthetic venous valve includes a coating of an anti-thrombotic agent to suppress blood clotting, an anti-proliferative agent to suppress excessive tissue ingrowth, or another drug. Alternatively, such an agent or drug can be embedded or dispersed into the material forming the frame and/or leaflets member. In some embodiments, a Heparin anti-coagulant or a nitric oxide coating is applied as a coating or dispersed or embedded into the matrix of the frame and/or leaflets member. In some embodiments, a Paclitaxol anti-proliferative drug is similarly included. In some embodiments, both an anti-thrombotic drug and an anti-proliferative drug are provided. In some embodiments, the polymer frame is partially hollowed out to provide a cavity or reservoir for holding a drug. Such a drug can be released by diffusion through the polymer frame or through a small orifice provided for drug release. The orifices may include a diffusion rate-limiting biomaterial, and may be either blood-facing or vessel-facing depending upon which tissue is intended to be therapeutically affected by the drug.

Figure 18:
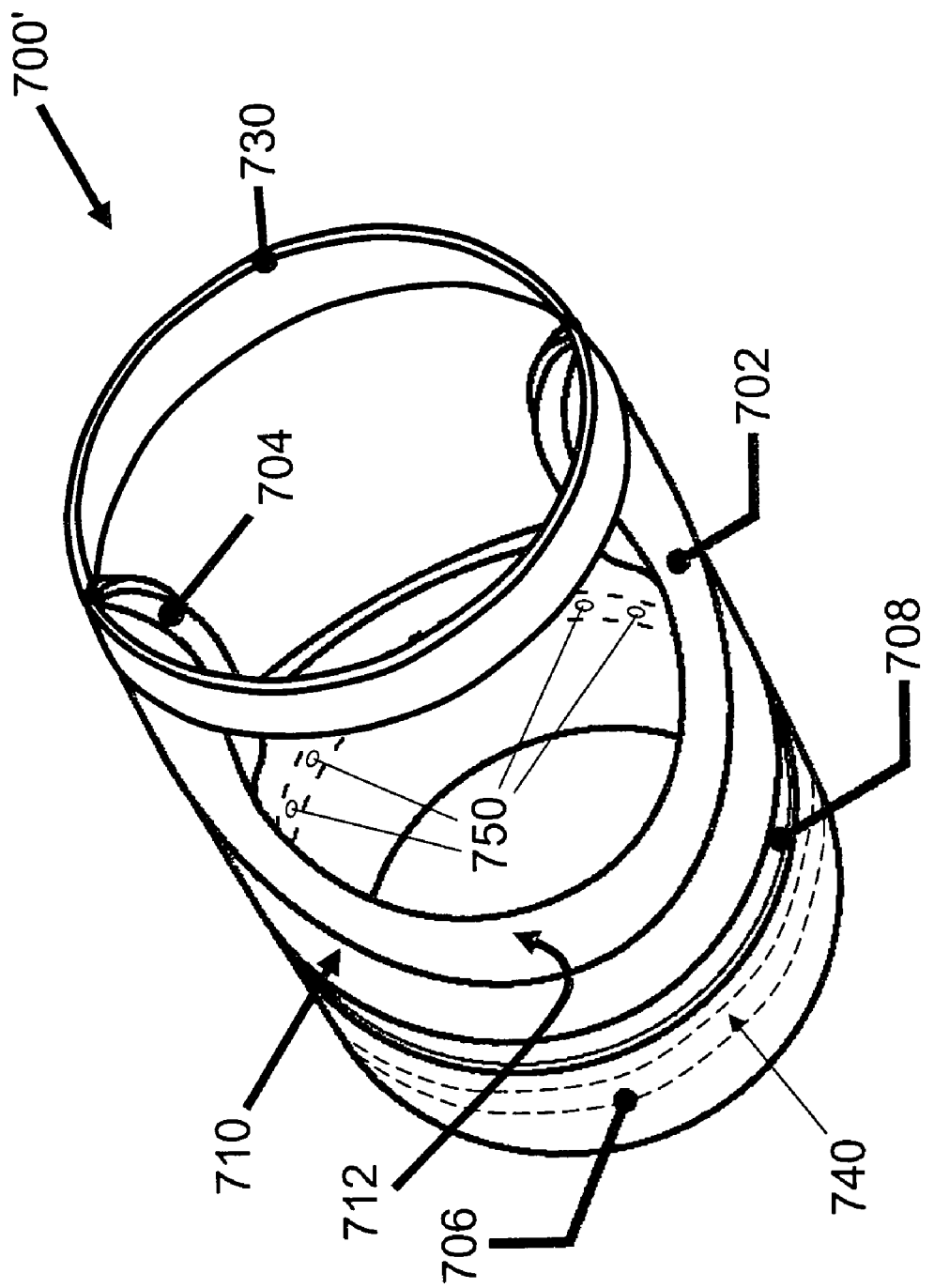
FIG. 18 shows a modified version of the frame of the third prototype valve, modified in that the frame shown in FIG. 18 includes a halo ring secured to the struts at the outflow end of the frame, and in that the frame shown in FIG. 18 includes a drug-containing cavity.
Figure 19B:
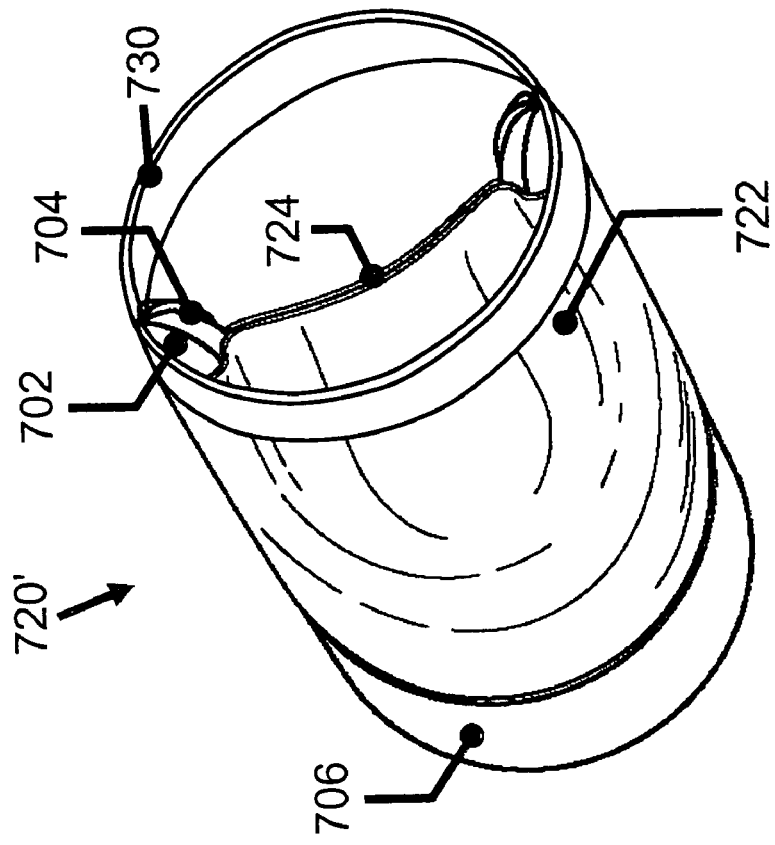
FIGS. 19A and 19B show perspective views of a prosthetic venous valve similar to the valve of FIGS. 17A and 17B, but including the frame of FIG. 18 rather than the frame of FIG. 16.
Figure 19A:
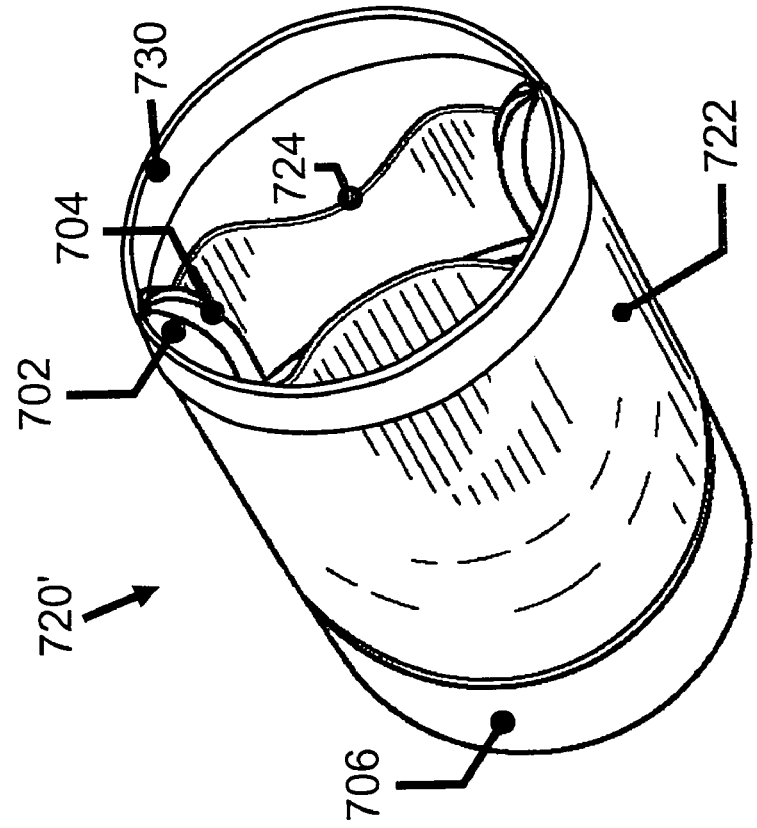

With reference to FIGS. 18 and 19A and 19B, a prosthetic venous valve 720' including a frame 700' is illustrated. The venous valve 720' is similar to the venous valve 720, except for having the modified frame 700'. The frame 700' is similar to the frame 700, but additionally includes a rigid or flexible halo ring 730 secured to the struts 702 at the outflow end of the frame 700'. The halo ring 730 suppresses contraction of the vein at the outflow end of the valve and thus maintains the vessel diameter at the outflow end to promote unmodified vein operation. The halo ring 730 also enhances structural sturdiness of the valve 700'. Although the halo ring 730 is positioned at the blood outflow end of the valve 700', in other contemplated embodiments the halo ring may be positioned elsewhere axially along the struts 702. It is also contemplated to include more than one halo ring, such as one halo ring approximately at the axial midpoint of the struts, and a second halo ring at the ends of the struts. The frame 700' further additionally includes an annular cavity 740 (hidden feature shown only by dashed lines in the perspective view of FIG. 18) suitable for containing an anti-thrombotic drug such as Heparin, or an anti-proliferative drug, or so forth. The anti-thrombotic drug is optionally released through small orifices 750 in the frame 700' that communicate with the annular cavity 740, or alternatively the orifices 750 may be omitted and the drug released by diffusion through the polymer or other material of the frame 700'. In some embodiments, the orifices 750 include rate-limiting plugs of a material through which the drug diffuses at a known rate.

Figure 20:
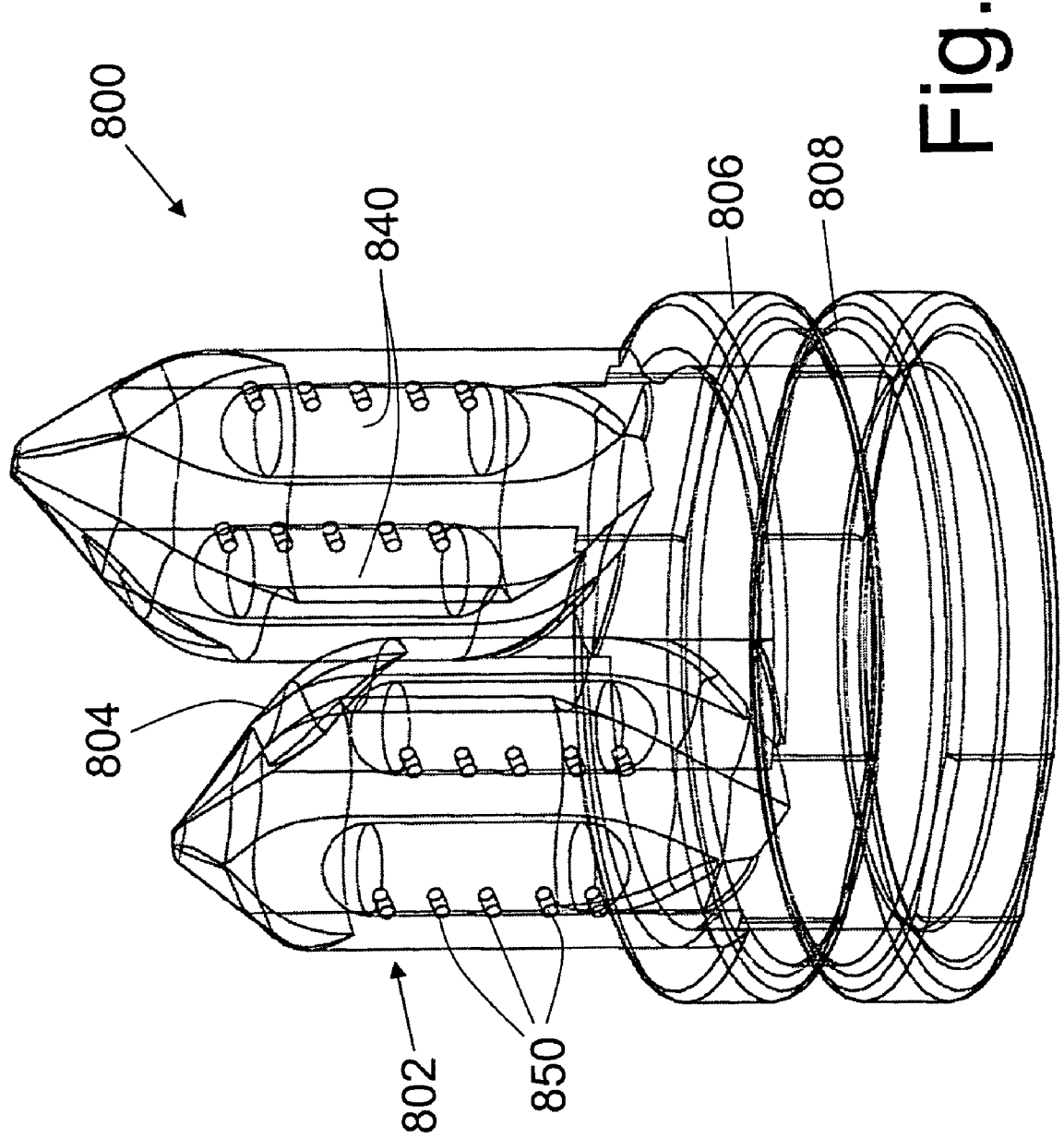
FIG. 20 shows a diagrammatic perspective view of a valve frame including drug delivery reservoirs in hollowed struts.

With reference to FIG. 20, another valve frame is illustrated, in which the drug delivery cavity is disposed in the struts. A frame 800 includes struts 802 having shaped inwardly oriented shaped flanges 804 and a base 806 including a suture ring 808. The struts 802 are partially hollowed out to define cavities 840 for containing anti-thrombotic, anti-proliferative, or other type of drug. Orifices 850 communicate with the cavities 740 to allow release of the drug at a controlled rate. Optionally, the orifices 750 include rate-limiting plugs of a material through which the drug diffuses at a known rate. Placing the drug delivery system in the struts rather than in the base (as is done in the example valve frame 700' of FIG. 18) is advantageous for delivery of an anti-thrombotic or anti-proliferative drug because it allows release of the drug locally near the struts which are particularly susceptible to problems caused by thrombosis or excessive tissue growth proliferation.

The disclosed venous valve prostheses are contemplated to be implanted into a living human or animal vein various ways. In some contemplated approaches, the vein is accessed surgically, cut open and the valve prosthesis implanted. Alternatively, a percutaneous placement can be used, in which the valve is inserted for example using a catheter. For percutaneous placement, it is advantageous to manufacture the valve frame of semi-flexible polymeric material so that the frame can deform slightly to promote percutaneous insertion. (Regardless of the implantation method, some flexibility in the frame is also expected to be advantageous to allow the valve to conform with natural distention or compression of the host vein.) Additionally or alternatively, the frame can be constructed as a collapsible structure in which, for example, one side of the frame is offset and aligned within the opposite side to reduce the profile of the valve for greater ease in percutaneous placement. Some suitable methods for surgical implantation and for percutaneous implantation of venous valve prostheses such as the venous valve prostheses disclosed herein are set forth in Acosta et al, Published Application No. 2002/0177894 A1, which is incorporated herein by reference in its entirety.

The valve prosthesis can be adhered to the vein wall in various ways. In some embodiments, a medical glue is used. In some embodiments, the valve is made of a polymer or other material that promotes tissue ingrowth, or includes a coating that promotes tissue ingrowth, such that the ingrown tissue secures the valve in place. In some embodiments, one or more suture loops are tightened around the outside of the vein to secure the valve in place. Various combinations of these techniques or other techniques can also be used.

The preferred embodiments have been described. Obviously, modifications and alterations will occur to others upon reading and understanding the preceding detailed description. It is intended that the appended claims be construed as including all such modifications and alterations insofar as they come within the scope of the appended claims or the equivalents thereof.

The appended claims follow.

The invention claimed is:

1. A prosthetic venous valve comprising:
a frame sized and configured to be implanted in a vein to replace a venous valve and including (i) a generally hollow base disposed at a blood inflow end, (ii) a plurality of struts connected with the base and extending generally parallel to a direction of forward flow of blood from the generally hollow base to a blood outflow end, and (iii) inwardly oriented flanges disposed at the blood outflow ends of the struts, the inwardly oriented flanges extending inwardly toward the center of the vein lumen; and
leaflets disposed in gaps between the struts and supported by the frame, the leaflets having free edges arranged to close into the vein lumen and meet to substantially seal against backflow of blood from the blood outflow end to the blood inflow end, the inwardly oriented flanges of the struts having curved surfaces configured to mate with proximate portions of the free edges of the leaflets to ensure sealing of the valve in the closed position substantially without buckling or pleating of the free edges of the leaflets;
wherein the curved surfaces of the inwardly oriented flanges of the struts include at least one of (i) curved surface portions having a constant radius of curvature and (ii) a semicircular portion continuing into a quarter-circular portion.

2. The prosthetic venous valve as set forth in claim 1, wherein the leaflets have curved free edges at the blood outflow end that are shaped relatively higher distal from the struts and relatively lower proximate to the struts to contact the curved surfaces of the inwardly oriented flanges and to contact each other along a cross-sectional plane in the closed position.

3. The prosthetic venous valve as set forth in claim 1, wherein at least a portion of the frame is partially hollowed out to define a cavity containing at least one drug, the cavity having orifices that are small compared with the cavity and that include rate-limiting plugs of a material through which the drug diffuses at a known rate to provide release of the drug from the cavity at a controlled rate.

4. The prosthetic venous valve as set forth in claim 3, wherein the drug comprises an anti-thrombotic or anti-proliferative agent.

5. The prosthetic venous valve as set forth in claim 3, wherein the orifices including rate limiting plugs are disposed on the struts to release the drug from the cavity locally near the struts.

6. The prosthetic venous valve as set forth in claim 1, wherein the leaflets comprise a generally tubular leaflets member that is tapered such that a cross-sectional dimension of the generally tubular leaflets members at the blood outflow end in the open position is smaller than or about 85% of a corresponding cross-sectional dimension of the generally tubular leaflets members at the blood inflow end.

7. The prosthetic venous valve as set forth in claim 6, wherein the tapering of the generally tubular leaflets member comprises:
a narrowing of a diameter of the generally tubular leaflets member from the blood inflow end to the blood outflow end such that the diameter at the blood outflow end is between about 70% and 85% of the diameter at the blood inflow end.

8. The prosthetic venous valve as set forth in claim 1, wherein each leaflet in the open position has a monotonically increasing longitudinal extent along a path starting at one of the two supporting neighboring struts and ending midway between the two supporting neighboring struts.

9. The prosthetic venous valve as set forth in claim 1, wherein the plurality of struts consists of two struts, and the plurality of leaflets consists of two leaflets.

10. The prosthetic venous valve as set forth in claim 9, wherein the two leaflets have free edges shaped to meet in a straight line along a diameter between the two struts in the closed position.

11. The prosthetic venous valve as set forth in claim 1, wherein the leaflets are wrapped around the outside of the plurality of struts.

12. The prosthetic venous valve as set forth in claim 1, wherein the leaflets are flexible leaflets.

13. A prosthetic venous valve comprising:
a frame sized and configured to be implanted in a vein to replace a venous valve and including (i) a generally hollow base disposed at a blood inflow end, (ii) a plurality of struts connected with the base and extending generally parallel to a direction of forward flow of blood from the generally hollow base to a blood outflow end, and (iii) inwardly oriented flanges disposed at the blood outflow ends of the struts, the inwardly oriented flanges extending inwardly toward the center of the vein lumen; and
leaflets disposed in gaps between the struts and supported by the frame, the leaflets having free edges arranged to close into the vein lumen and meet to substantially seal against backflow of blood from the blood outflow end to the blood inflow end, the inwardly oriented flanges of the struts having curved surfaces configured to mate with proximate portions of the free edges of the leaflets to ensure sealing of the valve in the closed position substantially without buckling or pleating of the free edges of the leaflets;
wherein the curved surfaces of the inwardly oriented flanges of the struts include curved surface portions having a constant radius of curvature.

14. The prosthetic venous valve as set forth in claim 13, wherein the leaflets are wrapped around the outside of the plurality of struts.

15. The prosthetic venous valve as set forth in claim 13, wherein the leaflets are flexible leaflets.

16. A prosthetic venous valve comprising:
a frame sized and configured to be implanted in a vein to replace a venous valve and including (i) a generally hollow base disposed at a blood inflow end, (ii) a plurality of struts connected with the base and extending generally parallel to a direction of forward flow of blood from the generally hollow base to a blood outflow end, and (iii) inwardly oriented flanges disposed at the blood outflow ends of the struts, the inwardly oriented flanges extending inwardly toward the center of the vein lumen; and leaflets disposed in gaps between the struts and supported by the frame, the leaflets having free edges arranged to close into the vein lumen and meet to substantially seal against backflow of blood from the blood outflow end to the blood inflow end, the inwardly oriented flanges of the struts having curved surfaces configured to mate with proximate portions of the free edges of the leaflets to ensure sealing of the valve in the closed position substantially without buckling or pleating of the free edges of the leaflets;

wherein the curved surfaces of the inwardly oriented flanges of the struts include a semicircular portion continuing into a quarter-circular portion.

* * * * *